United States Patent [19]
Tsujimoto et al.

[11] Patent Number: 6,071,845
[45] Date of Patent: Jun. 6, 2000

[54] CATALYST FOR PRODUCING CONJUGATED DIENE POLYMER

[75] Inventors: Nobuhiro Tsujimoto; Michinori Suzuki; Kei Tsukahara; Shigeru Ikai; Koji Imaoka; Yoshiyuki Kai; Jun Yamashita, all of Chiba, Japan

[73] Assignee: Ube Industries, Ltd., Yamaguchi, Japan

[21] Appl. No.: 08/761,697

[22] Filed: Dec. 6, 1996

[30] Foreign Application Priority Data

Dec. 8, 1995 [JP] Japan .................................. 7-320652
Jan. 26, 1996 [JP] Japan .................................. 8-011981
Apr. 5, 1996 [JP] Japan .................................. 8-083863

[51] Int. Cl.$^7$ .............................. C08F 4/68; C08F 36/04
[52] U.S. Cl. .................... 502/103; 502/114; 502/117; 502/129; 502/132; 502/152; 502/154; 502/155; 556/43; 526/160; 526/170; 526/943
[58] Field of Search .................... 502/114, 117, 502/128, 132, 152, 153, 155, 103; 556/43; 526/160, 170, 943

[56] References Cited

U.S. PATENT DOCUMENTS

| | | |
|---|---|---|
| 3,080,305 | 3/1963 | Gorsich . |
| 3,935,180 | 1/1976 | Sugiura et al. .................. 526/340.4 X |
| 3,983,183 | 9/1976 | Kampf . |
| 4,231,947 | 11/1980 | Schrock ............................... 556/43 X |
| 4,579,920 | 4/1986 | Tsujimoto et al. .................. 526/340 X |
| 4,752,597 | 6/1988 | Turner . |
| 4,791,180 | 12/1988 | Turner . |
| 4,808,561 | 2/1989 | Welborn, Jr. . |
| 4,897,455 | 1/1990 | Welborn, Jr. . |
| 5,132,380 | 7/1992 | Stevens et al. ..................... 526/134 X |
| 5,191,052 | 3/1993 | Welborn, Jr. . |
| 5,204,429 | 4/1993 | Kaminsky et al. . |
| 5,563,284 | 10/1996 | Frey et al. ............................. 556/43 X |
| 5,747,614 | 5/1998 | Takeuchi et al. ................... 526/170 X |

FOREIGN PATENT DOCUMENTS

| | | |
|---|---|---|
| 0 226 463 A1 | 6/1987 | European Pat. Off. . |
| 35-495 | 7/1955 | Japan . |
| 46-20494 | 6/1971 | Japan . |
| 46-020494 | 12/1971 | Japan . |
| 52-32912 | 8/1977 | Japan . |
| 55-129403 | 10/1980 | Japan . |
| 56-50894 | 12/1981 | Japan . |
| 59-232106 | 12/1984 | Japan . |
| 62-16201 | 4/1987 | Japan . |
| 63-501962 | 8/1988 | Japan . |
| 64-66216 | 3/1989 | Japan . |
| 1-501633 | 6/1989 | Japan . |
| 3-57128 | 8/1991 | Japan . |
| WO 94/01471 | 1/1994 | WIPO . |

OTHER PUBLICATIONS

"Metallocene Complexes of Group 4 Elements in the Polymerization of Monoolefins¹", *J.M.S.—Rev. Macromol. Chem. Phys.*, C34(3), pp. 439–514 (1994), Virendra Kumar Gupta, Sheo Satish, and Ishwar Singh Bhardwaj.

"Polimerizzazioni stereospecifiche di diolefine conjugate", La Chimica E L'Industria XL–5–1958, G. Natta, L. Porri, P. Corradini, D. Morero, pp. 362–371.

"Polymerizations of Butadiene and Isoprene with Transition Metals–Methylalumoxane Catalysts", International Rubber Conference 1995, Kobe, Japan, Oct. 23–27, 1995, pp. 176–179.

"Influence of Monomer Structure On Chemo– And Stereoselectivity of 1, 3–Diene Polymerization", Giovanni Ricci, Macromol. Symp. 89, pp. 383–392 (1995).

"Elastomers By Atactic Linkage of –Olefins Using Soluble Ziegler Catalysts", W. Kaminsky,* M. Schlobohm, Makromol. Chem., Macromol. Symp. 4, pp. 103–118 (1986).

"Polymerization of 1,3–dienes with catalysts based on mono–and bis–cyclopentadienyl derivatives of vanadium", Giovanni Ricci and Anna Panagia, Polymer, vol. 37, No. 2 pp. 363–365, (1996).

"Analysis of $^{13}$C NMR of Polybutadiene by Means of Low Molecular Weight Model Compounds", Hisaya Sato,* Kenji Takebayashi, and Yasuyuki Tanaka, Macromolecules, vol. 20, No., 1987, pp. 2418–2423.

"I, Über Darstellung und Reaktionen des Cyclopentadienyl-vanadin–trichlorids", Von K.–H. Thiele und L. Oswald, Z. anorg. allg. Chem., 423, pp. 231–234 (1976).

"Highly Oxidizing Organometallics: Physiocochemical Characterization of (Methycyclopentadienyl) vanadium (IV) Trichloride and Related Vanadium (III) and Titanium (III) Derivatives", David B. Morse, David N. Hendrickson,* Thomas B. Rauchfuss, * and Scott R. Wilson, Organometallics, vol. 7, No. 2, pp. 496–502 (1988).

"Preparation and Characterization of Mono–Cyclopentadi-enylvanadium Dihalide Bis–Phosphine Complexes; Crystal Structure of ($\eta^5$–C$_5$H$_5$)(VCl$_2$(PMe$_3$)$_2$", Journal of Organometallic Chemistry, vol. 255, pp. 193–204 (1983).

Giovanni Ricci and Anna Panagia, "Polymerization of 1,3–dienes With Catalysts Based On Mono– and bis–cyclopentadienyl Derivatives Of Vanadium" *Polymer*, vol. 37, pp. 363–365, 1996.

*Primary Examiner*—Fred Teskin
*Attorney, Agent, or Firm*—Akin, Gump, Strauss, Hauer & Feld, L.L.P.

[57] ABSTRACT

A catalyst obtained by contacting (A) a compound of a transition metal of the group V of the Periodic Table represented by formula (I):

$$R_n M(O)_m X_p \cdot L_a \quad (I)$$

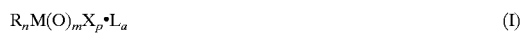

wherein M represents a transition metal of the group V of the Periodic Table; R represents a cyclopentadienyl group, a substituted cyclopentadienyl group, an indenyl group, a substituted indenyl group, a fluorenyl group or a substituted fluorenyl group; O represents an oxygen atom; X represents a hydrogen atom, a halogen atom, a hydrocarbon group having 1 to 20 carbon atoms, an alkoxy group, an aryloxy group or an amido group; L represents a Lewis basic compound; n, m, and p each represent an integer selected to make a combination of (n=1, m=1, p=2), (n=1, m=0, p=3), (n=2, m=0, p=1) or (n=1, m=0, p=2); and a represents 0, 1 or 2, and (B) at least one of (B1) an ionic compound comprising a non-coordinating anion and a cation and (B2) an aluminoxane, provided that the component (B) is an ionic compound comprising a non-coordinating anion and a cation (B1) when the combination of n, m, and p of the component (A) is (n=2, m=0, p=1) or (n=1, m=0, p=2).

10 Claims, No Drawings

CATALYST FOR PRODUCING CONJUGATED DIENE POLYMER

FIELD OF THE INVENTION

This invention relates to a novel catalyst comprising a compound of a transition metal of the group V of the Periodic Table, a process for producing a conjugated diene polymer using the catalyst, and polybutadiene having a specific structure.

BACKGROUND OF THE INVENTION

Catalyst systems comprising a metallocene complex of a transition metal, e.g., Ti, Zr or Hf, and an organoaluminum-oxy compound, e.g., methylaluminoxane, have been attracting attention as a catalyst for olefin polymerization. They have high activity particularly in copolymerization of ethylene and an α-olefin to provide excellent polymers having narrow molecular weight distribution and narrow composition distribution. These catalysts are described in detail in, e.g., *J.M.S.—Rev. Macromol. Chem. Phys.*, C34, No. 3, p. 439 (1994).

Catalyst systems containing a compound of a transition metal, e.g., Ti, V, Co, Ni or Nd, are known for catalysis in coordination anionic polymerization of conjugated dienes, such as butadiene and isoprene. For example, a method of using $VCl_3$—$AlR_3$ as a catalyst of conjugated diene polymerization is reported, e.g., in *Chim. e Ind.*, Vol. 40, p. 362 (1958). The result as reported, however, is production of crystalline polybutadiene having nearly 100% of a trans structure, and the catalyst has extremely low polymerization activity.

*International Rubber Conference Kobe, Preprint*, 25C-4 (1995) reports that $V(acac)_3$-methylaluminoxane provides polybutadiene comprising a cis structure, a trans structure, and a 1,2-structure in a proportion of 63%, 14%, and 21%, respectively, but the catalyst activity is still low.

Polymerization of conjugated diene by using a metallocene catalyst of the group IV transition metal (e.g., Ti or Zr) is reported in *Macromolecular Symposia*, Vol. 89, p. 383 (1995), in which a catalyst system containing cyclopentadienyltitanium trichloride $[(\eta^5C_5H_5)TiCl_3]$ is used. The activity of this catalyst system in conjugated diene polymerization is not deemed sufficient because the polymerization activity of $(\eta^5C_5H_5)TiCl_3$-methylaluminoxane, for instance, is, as reported, 100 g/mmol-Ti/hr at the most.

*Macromolecular Symposia*, Vol. 4, p. 103 (1986) reports copolymerization of ethylene and butadiene in the presence of a combination of bis(cyclopentadienyl)zirconium dichloride $[(\eta^5C_5H_5)_2ZrCl_2]$ and methylaluminoxane, but the report has no mention of the comonomer composition of the resulting polymer. Neither does the report refer to homopolymerization of butadiene. The reported catalyst activity is very low.

With regards to a polymerization catalyst comprising a metallocene compound of vanadium (V), the group V transition metal, JP-64-66216 (the term "JP-A" as used herein means an "unexamined published Japanese patent application") (U.S. Pat. No. 5,204,429), JP-W-63-501962 (the term "JP-W" as used herein means an "unexamined published international patent application") (U.S. Pat. Nos. 4,752,597 and 4,791,180), and JP-W-1-501633 (U.S. Pat. Nos. 5,191,052, 4,808,561 and 4,897,455) disclose a combination of a metallocene compound of vanadium and an aluminoxane as a catalyst for copolymerization of an olefin and a diene. These publications refer to bis(cyclopentadienyl)vanadium dichloride $[(\eta^5C_5H_5)_2VCl_2]$ as an illustrative example of the vanadium metallocene compounds without giving any working example using this particular compound.

JP-B-46-20494 (the term "JP-B" as used herein means an "examined published Japanese patent application") discloses a process for producing polybutadiene using a catalyst system comprising a cyclopentadienyl complex of vanadium, a halogen-containing organoaluminum compound, an oxygen-containing compound. $(C_5H_5)VCl_3$ is mentioned as an example of the cyclopentadienyl complex of vanadium, but its polymerization activity is problematically low. According to the disclosure, it is essential for the organoaluminum compound, which serves as a co-catalyst, to contain a halogen component. For example, a working example using $(C_5H_5)VCl_3$—$Al(i-Bu)_3/AlCl_3$ is given, but the polymerization activity attained in that example is 350 g/mmol-V/hr at the most.

*Polymer*, Vol. 37 (2), p. 363 (1966) describes a process for producing polybutadiene, in which a catalyst comprising a vanadium (III) compound, e.g., (substituted $C_5H_5$)$VCl_2 \cdot (PR_3)_2$ or (substituted $C_5H_5$)$_2VCl$, and methylaluminoxane is used to obtain polybutadiene of high cis structure having a 1,2-structure content of 10 to 20%. The polymerization activity of the catalyst is low however.

It is known that conjugated diene polymers take various microstructure depending on the polymerization catalyst used. While polybutadiene, for instance, is generally prepared by polymerization of 1,3-butadiene, polybutadiene as produced comprises different microstructures in its molecular chain, i.e., a structural unit produced through 1,4-addition (1,4-structure) and a structural unit produced through 1,2-addition (1,2-structure), due to the difference in mode of addition. The 1,4-structure is further divided into a cis-1,4-structure and a trans-1,4-structure. The 1,2-structure has a vinyl group as a side chain and can have an isotactic structure, an syndiotactic structure, and an atactic structure. The above-described macrostructure varies depending on the catalyst of polymerization, and polybutadiene species having different microstructures find their respective uses according to their characteristics. In particular, polybutadiene mainly comprising a cis structure and a moderate proportion of a 1,2-structure is expected as an impact modifier for plastics such as polystyrene.

Polybutadiene produced by using a butyllithium catalyst is known for use in high impact polystyrene (HIPS). Since it has a smaller content of a cis structure than the one produced by using a cobalt catalyst, an improvement in viscosity and the like has been demanded in the production of HIPS.

Cobalt catalyst systems that provide polybutadiene containing both a cis structure and a 1,2-structure include a catalyst system comprising a phosphate, an organoaluminum compound, water, and a cobalt compound and a catalyst system comprising an organoaluminum compound, water, and a cobalt dithiocarbamate compound as disclosed in JP-A-55-129403 and JP-A-59-232106. These catalysts sometimes provide polybutadiene having a low molecular weight, or they are not deemed to have sufficient catalyst activity.

JP-B-62-16201 discloses a process of using a catalyst system comprising a cobalt salt, a dialkylaluminum monohalide, and a dihydric alcohol. According to the disclosure, the resulting polybutadiene comprises 4 to 20% of a 1,2-structure, 75 to 95% of a cis-1,4-structure, and not more than 4% of a trans-1,4-structure, in which the content of 1,2-structures distributed at random is higher than the content of those connected to each other to form blocks, and is suitable for the production of HIPS.

For use as an impact modifier, polybutadiene must have a controlled molecular weight. For example, in the preparation of polybutadiene having a high cis content by using the above-described cobalt compound-organoaluminum compound catalyst system, it has been proposed to add a non-conjugated diene compound, such as cyclooctadiene, to the polymerization system as disclosed in JP-B-35-495.

However, addition of cyclooctadiene to the polymerization system comprising a metallocene complex of the group V transition metal unsuccessfully produces a sufficient effect for molecular weight reduction, only to lead to reduced polymerization activity.

JP-B-52-32912 (U.S. Pat. No. 3,983,183) and JP-B-56-50894 (U.S. Pat. No. 3,966,697) disclose a process for producing polybutadiene having a high 1,2-structure content by using a specific catalyst system. The Examples of the disclosures reveal that an increase in molecular weight of polybutadiene results in an increase in gel content.

A polybutadiene production system is liable to suffer from gelation in the polymer or the polymerization vessel. Gelation becomes conspicuous as the molecular weight increases. It is important for high-molecular weight polybutadiene, which is generally used as a mixture with an oil extender or a low-molecular polymer, to have an extremely low gel content formed during polymerization.

JP-B-3-57128 shows a process for producing polybutadiene having a cis-1,4-structure content of 50% or higher, a 1,2-structure content of 7 to 50%, an intrinsic viscosity of not less than 1, and a gel content of not more than 0.03%, which comprises using a catalyst system comprising a halogenated organoaluminum compound, a cobalt dithiocarbamate compound, water, and a free radical scavenger. However, the intrinsic viscosity of the polybutadiene obtained in the Examples is 2.5 at the most.

SUMMARY OF THE INVENTION

An object of the present invention is to provide a novel polymerization catalyst comprising a compound of a transition metal of the group V of the Periodic Table.

Another object of the invention is to provide a process for producing a controlled conjugated diene polymer using the above catalyst with high activity.

A further object of the invention is to provide polybutadiene having a specific structure which is effective as an impact modifier for HIPS.

Other objects and effects of the present invention will be apparent from the following description.

The present invention relates to a catalyst obtained by contacting (A) a compound of a transition metal of the group V of the Periodic Table represented by formula (I):

$$R_n M(O)_m X_p \cdot L_a \qquad (I)$$

wherein M represents a transition metal of the group V of the Periodic Table; R represents a cyclopentadienyl group, a substituted cyclopentadienyl group, an indenyl group, a substituted indenyl group, a fluorenyl group or a substituted fluorenyl group; O represents an oxygen atom; X represents a hydrogen atom, a halogen atom, a hydrocarbon group having 1 to 20 carbon atoms, an alkoxy group, an aryloxy group or an amido group; L represents a Lewis basic compound; n, m, and p each represent an integer selected to make a combination of (n=1, m=1, p=2), (n=1, m=0, p=3), (n=2, m=0, p=1) or (n=1, m=0, p=2); and a represents 0, 1 or 2, and (B) at least one of (B1) an ionic compound comprising a non-coordinating anion and a cation and (B2) an aluminoxane, provided that the component (B) is an ionic compound comprising a non-coordinating anion and a cation (B1) when the combination of n, m, and p of the component (A) is (n=2, m=0, p=1) or (n=1, m=0, p=2).

In a preferred embodiment, the catalyst obtained by contacting the components (A) and (B) and (C) an organic compound of the group I, II or III metal of the Periodic Table.

The present invention also relates to a catalyst comprising the components (A) and (B), preferably comprising components (A), (B) and (C).

The present invention further relates to a process for producing a conjugated diene polymer comprising a step of polymerizing a conjugated diene in the presence of the above-described catalysts.

DETAILED DESCRIPTION OF THE INVENTION

In formula (I) representing component (A) of the catalyst of the invention, the transition metal of the group V as represented by M includes the group Va transition elements, such as vanadium (V), niobium (Nb), and tantalum (Ta), with vanadium being preferred.

R represents a cyclopentadienyl group, a substituted cyclopentadienyl group, an indenyl group, a substituted indenyl group, a fluorenyl group or a substituted fluorenyl group.

Examples of substituents in the substituted cyclopentadienyl group, substituted indenyl group or substituted fluorenyl group include hydrocarbon groups which may contain a silicon atom, such as a methyl group, an ethyl group, a propyl group, an isopropyl group, an n-butyl group, an isobutyl group, a sec-butyl group, a t-butyl group, a hexyl group, a phenyl group, a benzyl group, and a trimethylsilyl group. A cyclopentadienyl ring as R and part of X may be bonded together via a linking group, such as a dimethylsilyl group, a dimethylmethylene group, a methylphenylmethylene group, a diphenylmethylene group, an ethylene group or a substituted ethylene group.

Examples of the substituted cyclopentadienyl group include methylcyclopentadienyl, benzylcyclopentadienyl, vinylcyclopentadienyl, 2-methoxyethylcyclopentadienyl, trimethylsilylcyclopentadienyl, t-butylcyclopentadienyl, ethylcyclopentadienyl, phenylcyclopentadienyl, 1,2-dimethylcyclopentadienyl, 1,3-dimethylcyclopentadienyl, 1,3-di(t-butyl)cyclopentadienyl, 1,2,3-trimethylcyclopentadienyl, 1,2,3,4-tetramethylcyclopentadienyl, pentamethylcyclopentadienyl, 1-ethyl-2,3,4,5-tetramethylcyclopentadienyl, 1-benzyl-2,3,4,5-tetramethylcyclopentadienyl, 1-phenyl-2,3,4,5-tetramethylcyclopentadienyl, 1-trimethylsilyl-2,3,4,5-tetramethylcyclopentadienyl, and 1-trifluoromethyl-2,3,4,5-tetramethylcyclopentadienyl groups.

Examples of the substituted indenyl group include 1,2,3-trimethylindenyl, heptamethylindenyl and 1,2,4,5,6,7-hexamethylindenyl groups.

R in formula (I) preferably represents a cyclopentadienyl group, a mono-substituted cyclopentadienyl group (e.g., ethylcyclopentadienyl group, a benzylcyclopentadienyl group or a methylcyclopentadienyl group) or an indenyl group.

X in formula (I) represents a hydrogen atom, a halogen atom, a hydrocarbon group having 1 to 20 carbon atoms, an alkoxy group or an amido group.

Examples of the halogen includes a fluorine atom, a chlorine atom, a bromine atom, and an iodine atom, with a chlorine atom being preferred.

Examples of the hydrocarbon group having 1 to 20 carbon atoms include straight-chain or branched aliphatic hydrocarbons, such as methyl, ethyl, propyl, isopropyl, butyl, t-butyl, neopentyl, hexyl and octyl groups; and aromatic hydrocarbon groups, such as phenyl, tolyl, naphthyl and benzyl groups. Hydrocarbon groups containing a silicon atom, such as trimethylsilylmethyl and bistrimethylsilylmethyl groups, are also included. Preferred of these hydrocarbon groups are methyl, benzyl and trimethylsilylmethyl groups.

Examples of the alkoxy group include methoxy, ethoxy, propoxy, butoxy, and t-butoxy groups. Additionally, amyloxy, hexyloxy, octyloxy, 2-ethylhexyloxy and thiomethoxy groups are also included. Examples of the aryloxy group include a phenoxy group. Preferred of these alkoxy groups and aryloxy groups are methoxy, t-butoxy, and phenoxy groups.

Examples of the amido group include dimethylamido, diethylamido, and diisopropylamido groups, with a dimethylamido group and a diethylamido group being preferred.

L in formula (I) represents a Lewis basic compound, i.e., a general organic or inorganic compound exhibiting Lewis basicity that can coordinate to a metal element with its counter electron. Compounds having no active hydrogen are preferred. Examples of such compounds include ethers, esters, ketones, amines, phosphines, and silyloxy compounds.

The compounds represented by formula (I) include $RMX_3$, $RM(O)X_2$, $R_2MX \cdot L_a$, $RMX_2 \cdot L_a$, and the like. In particular, vanadium compounds (where M is V), such as $RVX_3$, $RV(O)X_2$, $R_2VX \cdot La$, and $RVX_2 \cdot L_a$, are preferred.

Specific examples of RMX3 include the following compound groups (1) to (17):

(1) Cyclopentadienylvanadium trichloride;
(2) Mono-substituted cyclopentadienylvanadium trichloride:
Methylcyclopentadienylvanadium trichloride,
Ethylcyclopentadienylvanadium trichloride,
Propylcyclopentadienylvanadium trichloride,
Isopropylcyclopentadienylvanadium trichloride,
t-Butylcyclopentadienylvanadium trichloride,
Benzylcyclopentadienylvanadium trichloride,
(1,1-Dimethylpropyl)cyclopentadienylvanadium trichloride,
(1,1-Dimethylbenzyl)cyclopentadienylvanadium trichloride,
(1-Ethylpropyl)cyclopentadienylvanadium trichloride,
(1-Ethyl-1-methylpropyl)cyclopentadienylvanadium trichloride,
(Diethylbenzyl)cyclopentadienylvanadium trichloride,
(Trimethylsilylcyclopentadienyl)vanadium trichloride,
[Bis(trimethylsilyl)cyclopentadienyl]vanadium trichloride;
(3) 1,3-Substituted cyclopentadienylvanadium trichloride:
(1,3-Dimethylcyclopentadienyl)vanadium trichloride,
(1-Methyl-3-ethylcyclopentadienyl)vanadium trichloride,
(1-Methyl-3-propylcyclopentadienyl)vanadium trichloride,
[1-Methyl-3-bis(trimethylsilyl)silylcyclopentadienyl] vanadium trichloride,
(1-Methyl-3-phenylcyclopentadienyl)vanadium trichloride,
(1-Methyl-3-tolylcyclopentadienyl)vanadium trichloride,
[1-Methyl-3-(2,6-dimethylphenyl)cyclopentadienyl] vanadium trichloride,
(1-Methyl-3-butylcyclopentadienyl)vanadium trichloride;
(4) 1,2,3-Trisubstituted cyclopentadienylvanadium trichloride:
(1,2,3-Trimethylcyclopentadienyl)vanadium trichloride,
(1,2,3-Triethylcyclopentadienyl)vanadium trichloride,
(1,2,3-Triphenylcyclopentadienyl)vanadium trichloride;
(5) 1,2,4-Trisubstituted cyclopentadienylvanadium trichloride:
(1,2,4-Trimethylcyclopentadienyl)vanadium trichloride,
(1,2,4-Triethylcyclopentadienyl)vanadium trichloride,
(1,2,4-Triphenylcyclopentadienyl)vanadium trichloride;
(6) Tetrasubstituted cyclopentadienylvanadium trichloride:
(1,2,3,4-Tetramethylcyclopentadienyl)vanadium trichloride,
(1,2,3,4-Tetraphenylcyclopentadienyl)vanadium trichloride;
(7) Pentasubstituted cyclopentadienylvanadium trichloride:
(Pentamethylcyclopentadienyl)vanadium trichloride,
(1,2,3,4-Tetramethyl-5-phenylcyclopentadienyl) vanadium trichloride,
(1,2,3,4-Tetraphenyl-5-methylcyclopentadienyl) vanadium trichloride,
(Pentaphenylcyclopentadienyl)vanadium trichloride;
(8) Indenylvanadium trichloride;
(9) Substituted indenylvanadium trichloride:
(2-Methylindenyl)vanadium trichloride,
(2-Trimethylsilylindenyl)vanadium trichloride;
(10) The compounds (1) to (9) with one or two of the chlorine atoms displaced with an alkoxy group(s) (i.e., monoalkoxides or dialkoxides):
Cyclopentadienylvanadium t-butoxydichloride,
Cyclopentadienylvanadium isopropoxydichloride,
Cyclopentadienylvanadium dimethoxychloride,
Cyclopentadienylvanadium di-isopropoxychloride,
Cyclopentadienylvanadium di-t-butoxychloride,
Cyclopentadienylvanadium diphenoxychloride,
Cyclopentadienylvanadium isopropoxydichloride,
Cyclopentadienylvanadium t-butoxydichloride,
Cyclopentadienylvanadium phenoxydichloride;
(11) The compounds (1) to (10) with the chlorine atom(s) displaced with 1 to 3 methyl groups;
(12) Compounds in which R and X are bonded via a hydrocarbon group or a hydrocarbon silyl group:
(t-Butylamido)dimethylsilyl ($\eta^5$-cyclopentadienyl) vanadium dichloride,
(t-Butylamido)dimethylsilyl (trimethyl-$\eta^5$-cyclopentadienyl)vanadium dichloride,
(t-Butylamido)dimethylsilyl(tetramethyl-$\eta^5$-cyclopentadienyl)vanadium dichloride;
(13) The compounds (12) with their chlorine atom(s) displaced with 1 or 2 methyl groups;
(14) The compounds (12) with their chlorine atoms(s) displaced with 1 or 2 alkoxy groups;

(15) The monochloride compounds of the compounds (14) with the chlorine atom displaced with a methyl group;
(16) The compounds (1) to (10) with their chlorine atom(s) displaced with an amido group(s):
  (Cyclopentadienyl)tris(diethylamido)vanadium,
  (Cyclopentadienyl)tris(isopropylamido)vanadium,
  (Cyclopentadienyl)tris(n-octylamido)vanadium,
  (Cyclopentadienyl)bis(diethylamido)vanadium chloride,
  (Cyclopentadienyl)bis(isopropylamido)vanadium chloride,
  (Cyclopentadienyl)bis(n-octylamido)vanadium chloride,
  (Cyclopentadienyl)diethylamidovanadium dichloride,
  (Cyclopentadienyl)isopropylamidovanadium dichloride,
  (Cyclopentadienyl )n-octylamidovanadium dichloride;
(17) Fluorenylvanadium trichloride, in which the chlorine atom(s) thereof may be displaced with a methyl group(s), an alkoxy group(s) and/or an amido group(s).

Specific examples of $R_nM(O)X_2$ include the following compound groups (18) to (25):
(18) Cyclopentadienyloxovanadium dichloride;
  (19) Substituted cyclopentadienyloxyvanadium dichloride:
  Methylcyclopentadienyloxovanadium dichloride,
  1,3-Dimethylcyclopentadienyloxovanadium dichloride,
  1-Methyl-3-butylcyclopentadienyloxovanadium dichloride,
  Pentamethylcyclopentadienyloxovanadium dichloride,
  Trimethylsilylcyclopentadienyloxovanadium dichloride,
  1,3-Di(trimethylsilyl)cyclopentadienyloxovanadium dichloride,
  Indenyloxovanadium dichloride,
  2-Methylindenyloxovanadium dichloride,
  2-Trimethylsilylindenyloxovanadium dichloride,
  Fluorenyloxovanadium dichloride;
(20) The compounds (18) to (19) with 1 or 2 of the chlorine atoms displaced with 1 to 2 methyl groups:
(21) Compounds in which R and X are bonded via a hydrocarbon group or a hydrocarbon silyl group:
  Amidochloride compounds, e.g.,
  (t-butylamido)dimethylsilyl($\eta^5$-cyclopentadienyl)silaneoxovanadium chloride,
  (t-butylamido)dimethylsilyl(tetramethyl-$\eta^5$-cyclopentadienyl)silaneoxovanadium chloride; and
  these compounds with their chlorine atom substituted with a methyl group.
(22) Compounds in which X is an alkoxy group:
  Cyclopentadienyloxovanadium dimethoxide,
  Cyclopentadienyloxovanadium di-isopropoxide,
  Cyclopentadienyloxovanadium di-t-butoxide,
  Cyclopentadienyloxovanadium diphenoxide,
  Cyclopentadienyloxovanadium methoxychloride,
  Cyclopentadienyloxovanadium isopropoxychloride,
  Cyclopentadienyloxovanadium t-butoxychloride,
  Cyclopentadienyloxovanadium phenoxychloride;
(23) The compounds (22) with their chlorine atom displaced with a methyl group;
(24) Compounds in which X is an amido group:
  (Cyclopentadienyl)bis(diethylamido)oxovanadium,
  (Cyclopentadienyl)bis(di-isopropylamido)oxovanadium,
  (Cyclopentadienyl)bis(di-n-octylamido)oxovanadium;
(25) The compounds (24) with their amido group displaced with a methyl group.

Specific examples of $RMX_2 \cdot L_a$ include the following compound groups (26) to (30):
(26) Dichloride compounds, e.g., cyclopentadienylvanadium dichloride, methylcyclopentadienylvanadium dichloride, (1,3-dimethylcyclopentadienyl)vanadium dichloride, (1-methyl-3-butylcyclopentadienyl)vanadium dichloride, (pentamethylcyclopentadienyl)vanadium dichloride, (trimethylsilylcyclopentadienyl)vanadium dichloride, [1,3-di(trimethylsilyl)cyclolpentadienyl)vanadium dichloride, indenylvanadium dichloride, (2-methylindenyl)vanadium dichloride, (2-trimethylsilylindenyl)vanadium dichloride, and fluorenylvanadium dichloride; and compounds derived therefrom by displacing the chlorine atoms with methyl groups.
(27) Compounds in which R and X are connected via a hydrocarbon group or a silyl group, such as amidochloride compounds, e.g., (t-butylamido)dimethylsilyl($\eta^5$-cyclopentadienyl)vanadium chloride and (t-butylamido)dimethylsilyl(tetramethyl-$\eta$5-cyclopentadienyl)vanadium chloride; and compounds derived therefrom by displacing the chlorine atom with a methyl group.
(28) Alkoxide compounds, such as cyclopentadienylvanadium dimethoxide, cyclopentadienylvanadium di-isopropoxide, cyclopentadienylvanadium di-t-butoxide, cyclopentadienylvanadium diphenoxide, cyclopentadienylvanadium methoxychloride, cyclopentadienylvanadium isopropoxychloride, cyclopentadienylvanadium t-butoxychloride, and cyclopentadienylvanadium phenoxychloride; and compounds derived therefrom by displacing the chlorine atom with a methyl group.
(29) Bisamide compounds, such as (cyclopentadienyl)bis(diethylamido)vanadium, (cyclopentadienyl)bis(di-isopropylamido)vanadium, and (cyclopentadienyl)bis(di-n-octylamido)vanadium.
(30) Phosphine complexes, such as cyclopentadienylvanadium dichloride bistriethylphosphine complex, cyclopentadienylvanadium dichloride bistrimethylphosphine complex, (cyclopentadienyl)bis(di-isopropylamido)vanadium trimethylphosphine complex, and monomethylcyclopentadienylvanadium dichloride bistriethylphosphine complex.

Specific examples of $R_2MX \cdot L_a$ include the following compound groups (31) to (33):
(31) Chloride compounds, e.g., dicyclopentadienylvanadium chloride, bis(methylcyclopentadienyl)vanadium chloride, bis(1,3-dimethylcyclopentadienyl)vanadium chloride, bis(1-methyl-3-butylcyclopentadienyl)vanadium chloride, bis(pentamethylcyclopentadienyl)vanadium chloride, bis(trimethylsilylcyclopentadienyl)vanadium chloride, bis(1,3-di(trimethylsilyl)cyclopentadienyl) vanadium chloride, diindenylvanadium chloride, bis(2-methylindenyl)vanadium chloride, bis(2-trimethylsilylindenyl)vanadium chloride, and difluorenylvanadium chloride; and compounds derived therefrom by displacing the chlorine atom with a methyl group.
(32) Dicyclopentadienylvanadium methoxide, dicyclopentadienylvanadium isopropoxide, dicyclopentadienylvanadium t-butoxide, dicyclopentadienylvanadium phenoxide, dicyclopentadienyldiethylamidovanadium, dicyclopentadienyldi(isopropylamido)vanadium, and dicyclopentadienyldi(n-octylamido)vanadium.
(33) Compounds in which R and X are connected via a hydrocarbon group or a hydrocarbon silyl group, such as dimethylsilylbis($\eta^5$-cyclopentadienyl)vanadium chloride and dimethylsilylbis (tetramethyl-$\eta^5$-cyclopentadienyl)

vanadium chloride; and compounds derived therefrom by displacing the chlorine atom with a methyl group.

The compounds represented by $RVCl_3$ or $RV(O)Cl_2$ are synthesized through, for example, the following route.

$VCl_4$ or $VCl_3$ is reacted with an organometallic compound, e.g., RLi, RNa or RMgCl, to prepare $R_2VCl_2$ or $R_2VCl$, which is then treated with thionyl chloride $SOCl_2$ to synthesize $RVCl_3$. Treatment of $RVCl_3$ with oxygen gives $RV(O)Cl_2$.

Examples of the ionic compound composed of a non-coordinating anion and a cation as component (B) includes ionic compounds capable of reacting with the transition metal compound as component (A) to produce a cationic transition metal compound.

Examples of the non-coordinating anion includes tetraphenylborate, tetrakis(monofluorophenyl)borate, tetrakis(difluorophenyl)borate, tetrakis(trifluorophenyl) borate, tetrakis(tetrafluorophenyl)borate, tetrakis (pentafluorophenyl)borate, tetrakis(tetrafluoromethylpheyl) borate, tetratolylborate, tetraxylylborate, triphenyl (pentafluorophenyl)borate, tris(pentafluorophenyl) phenylborate, and tridecahydride 7,8-dicarbaundecaborate.

Examples of the cation includes a carbonium cation, an oxonium cation, an ammonium cation, a phosphonium cation, a cycloheptyltrienyl cation, and a ferrocenium cation having a transition metal.

Examples of the carbonium cation include tri-substituted carbonium cations, e.g., a triphenylcarbonium cation and a tri(substituted phenyl)carbonium cation (e.g., a tri (methylphenyl)carbonium cation and a tri(dimethylphenyl) carbonium cation.

Examples of the ammonium cation include trialkylammonium cations, such as a trimethylammonium cation, a triethylammonium cation, a tripropylammonium cation, a tributylammonium cation, a tri(n-butyl)ammonium cation; N,N-dialkylanilinium cations, such as an N,N-diethylanilinium cation, an N,N-diemthylanilinium cation and an N,N-dimethyl-2,4,6-trimethylanilinium cation; and dialkylammonium cations, such as a diisopropylammonium cation and a dicyclohexylammonium cation.

Examples of the phosphonium cation include triarylphosphonium cations, such as a triphenylphosphonium cation, a trimethylphenylphosphonium cation, and a tri (dimethylphenyl)phosphonium cation.

These non-coordinating anions and cations are combined arbitrarily to provide an appropriate ionic compound.

Of the ionic compounds, preferred are triphenylcarbonium tetrakis(pentafluorophenyl)borate, triphenylcarbonium tetrakis(tetrafluorophenyl)borate, N,N-dimethylanilinium tetrakis(pentafluorophenyl)borate, and 1,1'-dimethylferrocenium tetrakis(pentafluorophenyl) borate.

These ionic compounds may be used either individually or as a combination of two or more thereof.

An aluminoxane as component (B) is an organoaluminum-oxy compound obtained by contacting an organoaluminum compound with a condensing agent and includes an acyclic or cyclic aluminoxane represented by formula $(-Al(R')O-)_n$, wherein R' represents a hydrocarbon group having 1 to 10 carbon atoms, part of which may be substituted with a halogen atom and/or an alkoxy group; and n represents a degree of polymerization of 5 or more, preferably 10 or more). R' preferably represents a methyl, ethyl, propyl or isobutyl group, with a methyl group being preferred.

Examples of the organoaluminum compound which can be used as a starting material of the aluminoxane includes trialkylaluminum compounds, e.g., trimethylaluminum, triethylaluminum, and triisobutylaluminum, and mixtures thereof. Trimethylaluminum is particularly preferred.

An aluminoxane obtained from a mixture of trimethylaluminum and tributylaluminum can preferably be used. An aluminoxane having satisfactory solubility in aliphatic hydrocarbons is particularly suitable.

Typical examples of the condensing agent include water. In addition, arbitrary condensing agents causing condensation of trialkylaluminum compounds, such as adsorbed water of an inorganic substance or a diol, can also be used.

In the present invention, polymerization of a conjugated diene can be carried out in the presence of (C) an organometallic compound of the group I to III element of the Periodic Table in combination with components (A) and (B). Addition of component (C) is effective in increasing the polymerization activity of the catalyst of the invention. Examples of the organometallic compound of the group I to III element includes organoaluminum compounds, organolithium compounds, organomagnesium compounds, organozinc compounds and organoboron compounds.

Examples of the organometallic compound as component (C) are methyllithium, butyllithium, phenyllithium, benzyllithium, neopentyllithium, trimethylsilylmethyl lithium, bistrimethylsilylmethyl lithium, dibutylmagnesium, dihexylmagnesium, diethylzinc, dimethylzinc, trimethylaluminum, triethylaluminum, triisobutylaluminum, trihexylaluminum, trioctylaluminum, and tridecylaluminum.

Further, organic metal halides, such as ethylmagnesium chloride, butylmagnesium chloride, dimethylaluminum chloride, diethylaluminum chloride, sesquiethylaluminum chloride, and ethylaluminum dichloride; and organic metal hydrides, such as diethylaluminum hydride and sesquiethylaluminum hydride, are also useful as component (C). These organometallic compounds may be used either individually or as a combination of two or more thereof.

Where an ionic compound is used as component (B), the above-described aluminoxane may be used as component (C) in combination.

While the ratio of the catalyst components varies depending on various conditions, a preferred molar ratio of the transition metal compound as component (A) to the aluminoxane as component (B) is 1/1 to 1/10000, particularly 1/1 to 1/5000, and a preferred molar ratio of the transition metal compound as component (A) to the ionic compound as component (B) is 1/0.1 to 1/10, particularly 1/0.2 to 1/5. A preferred molar ratio of the transition metal compound as component (A) to the organometallic compound as component (C) is 1/0.1 to 1/1000, particularly 1/0.2 to 1/500.

While not limiting, the catalyst components are added, e.g., in the following order:

(1) Component (A) is added to a contact mixture of a conjugated diene monomer to be polymerized and component (B).

(2) A conjugated diene monomer to be polymerized, component (C), and an aluminoxane as component (B) are added in an arbitrary order, and component (A) is added to the contact mixture.

(3) An ionic compound as component (B) is added to a contact mixture of a conjugated diene monomer to be polymerized and component (C), and component (A) is then added thereto.

(4) A transition metal compound as component (A) is added to a contact mixture of a conjugated diene monomer to be polymerized and component (C), and component (B) is then added.

The order of addition (4) is preferred.

The catalyst of the invention and/or the individual catalyst component(s) thereof can be used as supported on an inorganic compound or an organic high polymeric compound.

Examples of inorganic compounds useful as a carrier preferably include inorganic oxides, inorganic chlorides, and inorganic hydroxides. These inorganic compounds may contain a small amount of a carbonate or a sulfate. Inorganic oxides, such as silica, alumina, magnesia, titania, zirconia, and calcia, are particularly preferred. The inorganic compounds are preferably used in the form of fine porous particles having an average particle size of 5 to 150 μm and a specific surface area of 2 to 800 m²/g. The inorganic compound particles can be used after heat treatment, e.g., at 100 to 800° C.

Examples of the organic high polymeric compounds useful as a carrier preferably include those having an aromatic ring, a substituted aromatic ring or a functional group, e.g., a hydroxyl group, a carboxyl group, an ester group or a halogen atom, in the side chain thereof. Examples of such compounds include α-olefin homo- or copolymers having the functional group obtained by chemical modification of polyethylene, polypropylene, polypolybutene, etc., homo- or copolymers of acrylic acid, methacrylic acid, vinyl chloride, vinyl alcohol, styrene, divinylbenzene, etc., and chemically modified polymers thereof. These organic high polymeric compounds are usually used in the form of spherical fine particles having an average particle size of 5 to 250 μm.

The language "a conjugated diene monomer to be polymerized" as used above means the whole amount or a part of a conjugated diene monomer to be polymerized. In the latter case, the "contact mixture" as referred to above can be mixed with the rest of the conjugated diene monomer.

Examples of the conjugated diene monomer are 1,3-butadiene, isoprene, 1,3-pentadiene, 2-ethyl-1,3-butadiene, 2,3-dimethylbutadiene, 2-methylpentadiene, 4-methylpentadiene, and 2,4-hexadiene. 1,3-Butadiene is particularly preferred.

These conjugated diene monomers may be used either individually or a combination of two or more thereof.

The monomer to be polymerized may be a mixture of a conjugated diene and a minor proportion of other monomers. Other monomers that may be present include acyclic monoolefins, e.g., ethylene, propylene, butene-1, butene-2, isobutene, pentene-1, 4-methylpentene-1, hexene-1, and octene-1; cyclic monoolefins, e.g., cyclopentene, cyclohexene, and norbornene; and/or aromatic vinyl compounds, e.g., styrene and α-methylstyrene; and non-conjugated diolefins, e.g., dicyclopentadiene, 5-ethylidene-2-norbornene, and 1,5-hexadiene.

The polymerization system is not particularly limited, and bulk polymerization, solution polymerization, gas phase polymerization, and the like can be adopted.

Useful solvents for solution polymerization include aromatic hydrocarbons, e.g., toluene, benzene, and xylene; aliphatic hydrocarbons, e.g., n-hexane, butane, heptane, and pentane; alicyclic hydrocarbons, e.g., cyclopentane and cyclohexane; olefinic hydrocarbons, e.g., 1-butene, cis-2-butene, and trans-2-butene; hydrocarbon solvents, such as mineral spirit, solvent naphtha and kerosine; and halogenated hydrocarbons, e.g., methylene chloride.

1,3-Butadiene as a monomer may also serve as a solvent in bulk polymerization. In particular, a mixture mainly comprising toluene, cyclohexane or cis-2-butene or a mixture comprising cis-2-butene and trans-2-butene is a preferred solvent.

Bulk polymerization or polymerization using a low-boiling hydrocarbon solvent is advantageous in that great energy for solvent recovery is not required.

It is possible to control the molecular weight of a conjugated diene polymer by carrying out the polymerization of a conjugated diene in the presence of hydrogen and the above-described catalyst. Hydrogen is used preferably in an amount of not more than 50 mmol or 1.2 l (at 20° C. under atmospheric pressure) per mole of a conjugated diene, particularly 0.05 to 20 mmol or 0.012 to 0.48 l (20° C., atmospheric pressure) per mole of a conjugated diene.

The polymerization is preferably carried out at −100 to 150° C., more preferably −100 to 100° C., particularly preferably −50 to 100° C., still particularly preferably −50 to 60° C., for 10 minutes to 12 hours, particularly 0.5 to 6 hours. After performing polymerization for a prescribed time period, the inner pressure of the reaction vessel is relieved according to necessity, and the polymer produced is worked up by washing, drying, and the like.

According to the process of the invention which uses the catalyst of the invention, polybutadiene having a 1,2-structure content of 4 to 30%, preferably 5 to 25%, still preferably 5 to 20%, a cis-1,4-structure content of 65 to 95%, preferably 70 to 95%, and a trans-1,4-structure content of not more than 5%, preferably not more than 4.5%, can be produced.

The polybutadiene having the above microstructure is suitable for use as an impact modifier for polystyrene.

The 1,2-structure content, cis-1,4-structure content, trans-1,4-structure content, and (1,2-structure)(1,4-structure) diad chain content can be obtained from the $^{13}$C-NMR spectrum in accordance with the analytical method described in *Macromoelcules*, Vol. 20, p. 2418 (1987).

If the 1,2-structure content is less than 4%, the graft efficiency of polybutadiene is reduced, and the effect of improving impact resistance of polystyrene is reduced. If the 1,2-structure content exceeds 30%, grafting of polybutadiene exceeds excessively, also resulting in reduction of the effect of improving impact resistance of polystyrene.

If the cis-1,4-structure content is out of the above range, the effect of improving impact resistance of polystyrene is reduced.

The present invention also provides polybutadiene having a 1,2-structure content of 4 to 30%, a cis-1,4-structure content of 65 to 95%, and a trans-1,4-structure content of not more than 5%, and whose B value represented by equation (a) is more than 1.0 and not more than 1.43.

$$B = P_{1,2-1,4}/(2 \times P_{1,2} \times P_{1,4}) \qquad (a)$$

wherein $P_{1,2}$ is a 1,2-structure content; $P_{1,4}$ is a 1,4-structure content; and $P_{1,2-1,4}$ is a (1,2-structure)(1,4-structure) diad chain content in the total diad chains.

B value is a parameter calculated from $P_{1,2}$, $P_{1,4}$, and $P_{1,2-1,4}$ and indicative of the distribution of (1,2-structure) and (1,4-structure) in a polybutadiene chain. When B is equal to 1, (1,2-structure) and (1,4-structure) are distributed completely at random. When B is larger than 1, diad chains in which (1,2-structure) and (1,4-structure) alternate are present in a larger proportion than in the completely random distribution. When B is smaller than 1, diad chains in which (1,2-structure) and (1,4-structure) are linked in respective blocks are present in a larger proportion than in the completely random distribution.

B value of the polybutadiene of the present invention is more than 1.0 and not more than 1.43, preferably more than 1.0 and not more than 1.25. This means that the proportion of diad chains in which (1,2-structure) and (1,4-structure)

alternate is larger than that of the diad chains of completely random polybutadiene. The polybutadiene of the invention shows improvement over conventional polybutadiene known for applicability to production of HIPS and exerts a more excellent effect as an impact modifier.

The invention further provides polybutadiene having a 1,2-structure content of 4 to 30%, a cis-1,4-structure content of 65 to 95%, a trans-1,4-structure content of not more than 5%, a gel content of not more than 0.1%, and an intrinsic viscosity [η] of 3 to 20 as measured in toluene at 30° C.

The above polybutadiene has a 1,2-structure content of 4 to 30%, preferably 5 to 25%, still preferably 7 to 15%, a cis-1,4-structure content of 65 to 95%, preferably 70 to 95%, still preferably 85 to 95%, and a trans-1,4-structure content of not more than 5%, preferably not more than 4.5%.

If the 1,2-structure content is less than 4%, the graft efficiency of polybutadiene is reduced, and the effect of improving impact resistance of polystyrene is reduced. If the 1,2-structure content exceeds 30%, grafting of polybutadiene exceeds excessively, also resulting in reduction of the effect of improving impact resistance of polystyrene.

If the cis-1,4-structure content is out of the above range, the effect of improving impact resistance of polystyrene is reduced.

The cis-1,4-structure, trans-1,4-structure and 1,2-structure are hereinafter sometimes referred to as "cis", "trans" and "vinyl", respectively.

The above polybutadiene is characterized by its gel content of not more than 0.1%, preferably not more than 0.05%. If the gel content is out of this range, the physical properties of polybutadiene or appearance of resultant molded articles are adversely affected.

The above polybutadiene is also characterized by its intrinsic viscosity [η] of 3 to 20, preferably 3 to 17, still preferably 5 to 15, as measured in toluene at 30° C.

The polybutadiene of the invention preferably have a number average molecular weight (Mn) of 300,000 to 2,000,000, particularly 600,000 to 1,500,000, a weight average molecular weight (Mw) of 750,000 to 4,000,000, particularly 1,000,000 to 3,000,000, as measured by gel-permeation chromatography (GPC), and a molecular weight distribution (Mw/Mn ratio) of 1.8 to 3.5, particularly 1.8 to 3.0.

The invention will now be illustrated in greater detail with reference to Examples and Comparative Examples, but it should be understood that the invention is not construed as being limited thereto.

In the Examples and Comparative Examples, the measurements of the polymers were conducted by the following manners.

The microstructure of the polymer was determined by analysis of infrared absorption spectrum. Specifically, the microstructure was determined from the intensity ratio of the absorptions at 740 cm$^{-1}$ (cis-1,4-structure), 967 cm$^{-1}$ (trans-1,4-structure) and 911 cm$^{-1}$ (1,2-structure).

The molecular weight was evaluated from results of GPC analysis using the standard polystyrene in terms of weight average molecular weight Mw, number average molecular weight Mn, and molecular weight distribution Mw/Mn.

The intrinsic viscosity [η] was measured.

The gel content was determined by dissolving about 2 g of a polymer produced in 200 ml of toluene, filtering the polymer solution through a metal net of 250 mesh, thoroughly washing the metal net with toluene, drying the metal net in vacuo at 80° C. for 5 hours, and obtaining an increase in weight of the net.

Examples 1 to 22 and Comparative Examples 1 to 4 concern RMX$_3$ compounds and polymerization using the same.

EXAMPLE 1

Synthesis of Cyclopentadienylvanadium Trichloride

The synthesis is in accordance with Z. Anorg. Allq. Chem., Vol. 423, p. 231 (1976).

To 134 ml (1.85 mol) of thionyl chloride was added 4.7 g (18.5 mmol) of bis(cyclopentadienyl)vanadium dichloride, followed by stirring at room temperature for 48 hours. Thionyl chloride was removed by evaporation under reduced pressure, and the residue was washed twice with a small amount of n-heptane. The residue was extracted twice with 100 ml portions of boiling chloroform. The extract was concentrated under reduced pressure and allowed to stand at room temperature to crystallize. The black purple crystals thus formed were collected by filtration, washed with toluene, and dried under reduced pressure to give 1.2 g (30%) of the title compound.

Elementary Analysis: Found (%): C, 26.8; H, 2.3; Cl, 47.5; Calcd. (%): C 27.00; H 2.27; Cl 47.82.

Polymerization of 1,3-Butadiene

A 1.5 l autoclave was purged with nitrogen, and 300 ml of toluene and 62 g of 1,3-butadiene were charged therein. To the mixture were added 0.8 ml of a toluene solution containing 2.5 mmol/ml-toluene of methylaluminoxane (MMAO, produced by Tosoh Akzo Corp.) as component (B) and 0.2 ml of a toluene solution containing 0.05 mmol/ml-toluene of cyclopentadienylvanadium trichloride (CpVCl$_3$) as component (A), and polymerization reaction was carried out at 40° C. for 60 minutes. After completion of polymerization, unreacted 1,3-butadiene was released from the autoclave, and an antioxidant was added to the reaction mixture. The reaction mixture was poured into ethanol, and the thus precipitated polymer was collected, washed, filtered, and dried. The reaction results are shown in Table 2 below.

The values of "catalytic activity" used in Examples and Comparative Examples were those obtained from calculation of the yielded amount of the polymer, the reaction time and the vanadium amount in the catalyst used.

EXAMPLES 2 TO 6

1,3-Butadiene was polymerized in the same manner as in Example 1, except for altering the conditions as shown in Table 1 below. The reaction results are shown in Table 2.

EXAMPLE 7

1,3-Butadiene was polymerized in the same manner as in Example 1, except for adding the catalyst components in the order of CpVCl$_3$ and MMAO. The reaction results are shown in Table 2.

EXAMPLE 8

1,3-Butadiene was polymerized in the same manner as in Example 7, except for altering the conditions as shown in Table 1 below. The reaction results are shown in Table 2.

EXAMPLE 9

A 1.5 l autoclave was purged with nitrogen, and 300 ml of toluene and 62 g of 1,3-butadiene were charged therein. To the mixture were added 0.5 ml of toluene solution containing 1 mmol/ml-toluene of triisobutylaluminum (TIBAL) as component (C), 1.5 ml of a toluene solution containing 0.005 mmol/ml-toluene of triphenylcarbonium tetrakis(pentafluorophenyl)borate (Ph$_3$CB(C$_6$F$_5$)$_4$) as component (B), and 0.1 ml of a toluene solution containing 0.05 mmol/ml-toluene of cyclopentadienylvanadium trichloride (CpVCl$_3$) as component (A), and polymerization reaction was conducted at 40° C. for 20 minutes. The reaction results are shown in Table 2.

EXAMPLE 10

1,3-Butadiene was polymerized in the same manner as in Example 9, except for altering the conditions as shown in Table 1 below. The reaction results are shown in Table 2.

EXAMPLE 11

1,3-Butadiene was polymerized under the conditions shown in Table 1 in the same manner as in Example 9, except for using 2 mmol of MMAO as component (C). The reaction results are shown in Table 2.

COMPARATIVE EXAMPLE 1

1,3-Butadiene was polymerized in the same manner as in Example 1, except for using acetylacetonatovanadium (III) (V(acac)$_3$) as component (A) and MMAO as component (B) and changing the reaction conditions as shown in Table 3 below. The reaction results are shown in Table 4.

COMPARATIVE EXAMPLE 2

1,3-Butadiene was polymerized in the same manner as in Example 1, except for using triethylaluminum (TEA) as component (B) and changing the reaction conditions as shown in Table 3 below. The reaction results are shown in Table 4.

COMPARATIVE EXAMPLE 3

1,3-Butadiene was polymerized in the same manner as in Example 1, except for using ethylaluminum sesquichloride (EASC) as component (B) and changing the reaction conditions as shown in Table 3 below. The reaction results are shown in Table 4.

COMPARATIVE EXAMPLE 4

1,3-Butadiene was polymerized in the same manner as in Example 1, except for using bis(cyclopentadienyl)vanadium dichloride (Cp$_2$VCl$_2$) as component (A) and changing the reaction conditions as shown in Table 3 below. The reaction results are shown in Table 4.

EXAMPLES 12 TO 16

1,3-Butadiene was polymerized in the same manner as in Example 1, except for using 300 ml of cyclohexane as a polymerization solvent (cyclohexane and 1,3-butadiene made 400 ml), CpVCl$_3$ as component (A), and Ph$_3$CB(C$_6$F$_5$)$_4$ as component (B), and triisobutylaluminum as component (C), and changing the reaction conditions as shown in Table 5 below. The reaction results are shown in Table 6.

EXAMPLE 17

1,3-Butadiene was polymerized in the same manner as in Example 12, except for using triethylaluminum as component (C) and changing the reaction conditions as shown in Table 5. The reaction results are shown in Table 6.

EXAMPLE 18

1,3-Butadiene was polymerized in the same manner as in Example 12, except for using MMAO as component (B), using no component (C), and changing the reaction conditions as shown in Table 5. The reaction results are shown in Table 6.

EXAMPLES 19 TO 22

1,3-Butadiene was polymerized in the same manner as in Example 12, except that a mixed solvent of cyclohexane and a cis-2-butene/trans-2-butene mixture (about 80/20 by weight) was used as a polymerization solvent (the mixed solvent and 1,3-butadiene made 400 ml), CpVCl$_3$ as component (A), and Ph$_3$CB(C$_6$F$_5$)$_4$ as component (B), and triisobutylaluminum as component (C), and changing the reaction conditions as shown in Table 7 below. The reaction results are shown in Table 8 below.

TABLE 1

| Example No. | Component (A) (mmol) | Component (B) (mmol) | Component (C) (mmol) | Reaction Temp. (° C.) | Reaction Time (min) |
|---|---|---|---|---|---|
| 1 | 0.01 | 2 | — | 40 | 60 |
| 2 | 0.01 | 5 | — | 40 | 60 |
| 3 | 0.01 | 10 | — | 40 | 60 |
| 4 | 0.01 | 5 | — | 50 | 60 |
| 5 | 0.01 | 5 | — | 30 | 30 |
| 6 | 0.01 | 2 | — | 20 | 40 |
| 7 | 0.015 | 15 | — | 40 | 60 |
| 8 | 0.015 | 30 | — | 40 | 60 |
| 9 | 0.005 | 0.0075 | 0.5 | 40 | 20 |
| 10 | 0.005 | 0.01 | 0.5 | 40 | 20 |
| 11 | 0.01 | 0.01 | 2 | 40 | 30 |

TABLE 2

| Example No. | Yield (g) | Catalytic Activity (g/mmol-V.hr) | Microstructure (%) | | |
|---|---|---|---|---|---|
| | | | cis | trans | vinyl |
| 1 | 13.3 | 1330 | 90.5 | 0.6 | 8.9 |
| 2 | 36.0 | 3600 | 90.2 | 1.2 | 8.6 |
| 3 | 32.5 | 3250 | 90.7 | 0.9 | 8.4 |
| 4 | 16.8 | 1680 | 89.8 | 1.5 | 8.7 |
| 5 | 37.4 | 7480 | 89.8 | 1.6 | 8.6 |
| 6 | 47.9 | 7185 | 90.1 | 1.6 | 8.3 |
| 7 | 36.4 | 2427 | 90.7 | 1.0 | 8.3 |
| 8 | 30.6 | 2040 | 91.1 | 0.6 | 8.3 |
| 9 | 36.8 | 22080 | 88.0 | 2.0 | 10.0 |
| 10 | 35.8 | 21420 | 88.0 | 2.0 | 10.0 |
| 11 | 42.9 | 8580 | 88.0 | 2.0 | 10.0 |

TABLE 3

| Comparative Example No. | Component (A) (mmol) | Component (B) (mmol) | Component (C) (mmol) | Reaction Temp. (° C.) | Reaction Time (min) |
|---|---|---|---|---|---|
| 1 | 0.1 | 40 | — | 20 | 60 |
| 2 | 0.1 | 15 | — | 40 | 60 |
| 3 | 0.1 | 15 | — | 40 | 60 |
| 4 | 0.01 | 10 | — | 40 | 60 |

TABLE 4

| Comparative Example No. | Yield (g) | Catalytic Activity (g/mmol-V.hr) | Microstructure (%) | | |
|---|---|---|---|---|---|
| | | | cis | trans | vinyl |
| 1 | 2.3 | 23 | 55.5 | 33.6 | 10.9 |
| 2 | 0 | 0 | — | — | — |

TABLE 4-continued

| Comparative Example No. | Yield (g) | Catalytic Activity (g/mmol-V.hr) | Microstructure (%) | | |
|---|---|---|---|---|---|
| | | | cis | trans | vinyl |
| 3 | 0.8 | 8 | 84.0 | 3.4 | 12.6 |
| 4 | 1.4 | 140 | 90.0 | 1.4 | 8.6 |

TABLE 5

| Example No. | Component (A) (mmol) | Component (B) (mmol) | Component (C) (mmol) | Reaction Temp. (° C.) | Reaction Time (min) |
|---|---|---|---|---|---|
| 12 | 0.005 | 0.0075 | 0.25 | 40 | 60 |
| 13 | 0.005 | 0.0075 | 0.5 | 40 | 60 |
| 14 | 0.005 | 0.01 | 0.25 | 40 | 60 |
| 15 | 0.005 | 0.0125 | 0.25 | 40 | 60 |
| 16 | 0.005 | 0.01 | 0.25 | 60 | 60 |
| 17 | 0.005 | 0.01 | 0.25 | 40 | 60 |
| 18 | 0.01 | 5 | — | 40 | 60 |

TABLE 6

| Example No. | Yield (g) | Catalytic Activity g/mmol-V.hr | Microstructure (%) | | | Mw (×10⁶) | Mn (×10⁶) | Mw/Mn |
|---|---|---|---|---|---|---|---|---|
| | | | cis | trans | vinyl | | | |
| 12 | 22.4 | 4480 | 86.8 | 1.1 | 12.1 | 2.94 | 1.42 | 2.07 |
| 13 | 16.0 | 3200 | 87.2 | 1.0 | 11.8 | 2.33 | 0.96 | 2.42 |
| 14 | 28.1 | 5620 | 86.7 | 1.3 | 12.0 | 3.17 | 1.58 | 2.01 |
| 15 | 17.0 | 3400 | 86.7 | 1.2 | 12.1 | 2.77 | 1.43 | 1.94 |
| 16 | 35.7 | 7140 | 86.0 | 2.0 | 12.0 | 1.53 | 0.72 | 2.12 |
| 17 | 47.0 | 9400 | 86.7 | 1.6 | 11.7 | 2.39 | 1.02 | 2.34 |
| 18 | 33.9 | 3390 | 89.5 | 1.2 | 9.3 | 2.20 | 1.00 | 2.20 |

Examples 23 to 32 and Comparative Examples 5 and 6 relate to $RM(O)X_2$ compounds and polymerization using the same.

EXAMPLE 23

Synthesis of Transition Metal Compound

Cyclopentadienyloxovanadium dichloride ($VO(Cp)Cl_2$) was synthesized in accordance with *Organometallics*, Vol. 7, pp. 496–502 (1988) in the form of a solution in toluene.

Polymerization of Butadiene

To 200 ml of toluene was added a toluene solution containing 1 mmol of methylaluminoxane (MMAO, produced by Tosoh-Akzo Corp.), and the resulting solution was maintained at 40° C. To the solution was added 32 ml of butadiene, and the above-prepared toluene solution of 1 μmol of $VO(Cp)Cl_2$ was added thereto to conduct polymerization for 1 hour. The polymerization reaction was stopped by addition of an HCl-containing ethanol solution, and the reaction mixture was filtered and dried to give a white butadiene polymer. The catalytic activity was 6,200 g/mmol-V.hr. The resulting polybutadiene had a cis-structure content of 89.9%, a trans-structure of 1.8%, a vinyl structure (1,2-structure) content of 8.3%, an Mw of 2,540,000, and an Mw/Mn ratio of 2.06.

EXAMPLE 24

Polymerization of Butadiene

Butadiene was polymerized in the same manner as in Example 23, except for using 2 mmol of methylaluminoxane. The catalytic activity was 7,500 g/mmol-V.hr. The resulting polybutadiene had a cis-structure of 89.9%, a trans-structure of 1.6%, a vinyl structure (1,2-structure) of 8.5%, an Mw of 2,730,000, and Mw/Mn ratio of 3.34.

EXAMPLE 25

Polymerization of Butadiene

Butadiene was polymerized in the same manner as in Example 24, except for using 5 mmol of methylaluminoxane. The catalytic activity was 9,000 g/mmol-V.hr. The resulting polybutadiene had a cis-structure of 89.9%, a trans-structure of 1.6%, a vinyl structure (1,2-structure) of 8.5%, an Mw of 2,826,000, and Mw/Mn ratio of 2.82.

TABLE 7

| Example No. | Cyclohexane (wt %) | C4 Fraction* (wt %) | 1,3-Butadiene (wt % (g)) | Component (A) (mmol) | Component (B) (mmol) | Component (C) (mmol) | Reaction Temp. (° C.) | Reaction Time (min) |
|---|---|---|---|---|---|---|---|---|
| 19 | 70 | 9 | 21 (61) | 0.005 | 0.0075 | 0.5 | 40 | 60 |
| 20 | 59 | 21 | 20 (57) | 0.005 | 0.0075 | 0.5 | 40 | 60 |
| 21 | 49 | 29 | 22 (60) | 0.005 | 0.0075 | 0.5 | 40 | 60 |
| 22 | 41 | 38 | 21 (56) | 0.005 | 0.0075 | 0.5 | 40 | 60 |

Note: *Cis-2-butene (ca. 80 wt %)/trans-2-butene (ca. 20 wt %) mixture

TABLE 8

| Example No. | Yield (g) | Catalytic Activity (g/mmol-V.hr) | Microstructure (%) | | | Mw (× 10⁶) | Mn (× 10⁶) | Mw/Mn Ratio |
|---|---|---|---|---|---|---|---|---|
| | | | cis | trans | vinyl | | | |
| 19 | 19.2 | 3840 | 86.8 | 1.2 | 12.0 | 2.12 | 0.95 | 2.23 |
| 20 | 17.3 | 3460 | 86.9 | 1.1 | 12.0 | 2.16 | 1.02 | 2.11 |
| 21 | 16.4 | 3280 | 86.8 | 1.1 | 12.1 | 2.13 | 0.97 | 2.19 |
| 22 | 14.5 | 2900 | 86.4 | 1.2 | 12.4 | 2.08 | 0.86 | 2.41 |

EXAMPLE 26
Polymerization of Butadiene

To 200 ml of toluene was added a toluene solution containing 0.2 mmol of triisobutylaluminum, and the solution was kept at 40° C. To the solution was added 32 ml of butadiene, and 1.5 μmol of $Ph_3CB(C_6F_5)_4$ and a toluene solution of 1.0 μmol of $VO(Cp)Cl_2$ prepared in Example 23 were added thereto to conduct polymerization for 1 hour. The polymerization reaction was stopped by addition of an HCl-containing ethanol solution, and the reaction mixture was filtered and dried to give white polybutadiene having a cis-structure content of 88.9%, a trans-structure of 1.7%, a vinyl (1,2)-structure of 9.4%, an Mw of 2,917,000, and an Mw/Mn ratio of 2.96. The catalytic activity was 10,200 g/mmol.V.hr.

EXAMPLE 27
Polymerization of Butadiene

To 200 ml of toluene was added a toluene solution containing 0.2 mmol of triisobutylaluminum, and the solution was kept at 40° C. To the solution was added 32 ml of butadiene, and 1.5 μmol of $Ph_3CB(C_6F_5)_4$ was then added thereto. A toluene solution containing 1.0 μmol of $VO(Cp)Cl_2$ prepared in Example 23 was added to the mixture while feeding hydrogen at a rate of 5 ml/min to conduct polymerization for 1 hour. The polymerization reaction was stopped by addition of an HCl-containing ethanol solution, and the reaction mixture was filtered and dried to give white polybutadiene having a cis-structure content of 87.2%, a trans-structure of 3.6%, a vinyl (1,2)-structure of 9.2%, an Mw of 502,000, and an Mw/Mn ratio of 1.59. The catalytic activity was 8,100 g/mmol.V.hr.

EXAMPLE 28
Polymerization of Butadiene

Butadiene was polymerized in the same manner as in Example 27, except for feeding hydrogen at a rate of 20 ml/min. The polymerization reaction was stopped by addition of an HCl-containing ethanol solution, and the reaction mixture was filtered and dried to give white polybutadiene having a cis-structure content of 86.7%, a trans-structure of 5.9%, a vinyl (1,2)-structure of 7.4%, an Mw of 19,000, and an Mw/Mn ratio of 2.86. The catalytic activity was 5,200 g/mmol.V.hr.

EXAMPLES 29 TO 32

Butadiene was polymerized in the same manner as in Example 9, except for using $VO(Cp)Cl_2$ was used as component (A) in place of $CpVCl_3$, triethylalumium was used as component (C) in place of TIBAL, and the conditions were changed to those shown in Table 9. The reaction results are shown in Table 10.

TABLE 9

| Example No. | Component (A) (mmol) | Component (B) (mmol) | Component (C) (mmol) | Reaction Temp. (° C.) | Reaction Time (min) |
|---|---|---|---|---|---|
| 29 | 0.005 | 0.0075 | 0.75 | 40 | 20 |
| 30 | 0.005 | 0.0075 | 1.0 | 40 | 20 |
| 31 | 0.005 | 0.0075 | 1.45 | 40 | 20 |
| 32 | 0.005 | 0.0075 | 2.0 | 40 | 20 |

TABLE 10

| Example No. | Yield (g) | Catalytic Activity (g/mmol-V.hr) | Microstructure (%) cis | trans | vinyl | [η] | Mw (× 10⁶) | Mn (× 10⁶) | Mw/Mn |
|---|---|---|---|---|---|---|---|---|---|
| 29 | 41.3 | 24780 | 87.9 | 2.2 | 9.9 | 9.15 | 1.97 | 0.93 | 2.12 |
| 30 | 42.1 | 25260 | 88.0 | 2.1 | 9.9 | 9.00 | 1.98 | 0.94 | 2.11 |
| 31 | 39.9 | 23940 | 88.4 | 1.9 | 9.7 | 9.65 | 1.83 | 0.80 | 2.29 |
| 32 | 30.1 | 18060 | 88.8 | 1.6 | 9.6 | 8.59 | 1.78 | 0.89 | 2.00 |

EXAMPLES 33 TO 34

Butadiene was polymerized in the same manner as in Example 17, except for using $VO(Cp)Cl_2$ was used as component (A) in place of $CpVCl_3$ and the conditions were changed to those shown in Table 11. The reaction results are shown in Table 12.

TABLE 11

| Example No. | Component (A) (mmol) | Component (B) (mmol) | Component (C) (mmol) | Reaction Temp. (° C.) | Reaction Time (min) |
|---|---|---|---|---|---|
| 33 | 0.005 | 0.01 | 0.5 | 40 | 60 |
| 34 | 0.005 | 0.01 | 0.75 | 40 | 60 |

TABLE 12

| Example No. | Yield (g) | Catalytic Activity (g/mmol-V.hr) | Microstructure (%) cis | trans | vinyl | Mw (× 10⁶) | Mn (× 10⁶) | Mw/Mn |
|---|---|---|---|---|---|---|---|---|
| 33 | 38.4 | 7680 | 87.2 | 1.1 | 11.7 | 2.07 | 1.07 | 1.94 |
| 34 | 38.1 | 7620 | 87.1 | 1.3 | 11.6 | 1.75 | 0.84 | 2.08 |

COMPARATIVE EXAMPLE 5
Polymerization of Butadiene

Butadiene was polymerized in the same manner as in Example 23, except for using 1.0 μmol of vanadyl trichloride (VOCl$_3$), but substantially in vain.

COMPARATIVE EXAMPLE 6
Polymerization of Butadiene

Butadiene was polymerized in the same manner as in Example 25, except for using 1.0 μmol of vanadyl trichloride (VOCl$_3$), but substantially in vain.

Examples 35 to 39 relate to RMX$_3$ having a substituent and polymerization using the same.

EXAMPLE 35
Preparation of Transition Metal Compound ($\eta^5$C$_5$H$_4$(SiMe$_3$)VCl$_3$)

In 40 ml of tetrahydrofuran (THF) was dissolved 7.3 g (40 mmol) of C$_5$H$_5$(SiMe$_3$) in a nitrogen stream, and the solution was cooled to −78° C. To the solution was added dropwise 29.8 ml (48 mmol) of a 1.61M hexane solution of n-BuLi. The reaction mixture was concentrated, and the residue was washed with hexane. The solid was dissolved in 40 ml of THF, and the solution was added dropwise to 20 ml of a toluene solution containing 2.3 ml (22 mmol) of VCl$_4$ at a THF refluxing temperature, followed by stirring at room temperature for 10 hours. The solvent was removed, and 100 ml of toluene was added to the residue. After stirring, LiCl was removed by filtration. The filtrate was concentrated, and to the residue was added an equivalent weight of hexane, followed by cooling to −78° C. The precipitated deep blue crystals were separated by filtration. To the crystals was added 50 ml of thionyl chloride, and the mixture was stirred at room temperature for 10 hours. After completion of the reaction, thionyl chloride was removed by evaporation under reduced pressure. To the residue was added 100 ml of toluene, followed by filtration. The filtrate was concentrated, 50 ml of hexane was added thereto, and deep purple crystals were obtained at −78° C. The crystals were collected by filtration and dried at room temperature under reduced pressure. The resulting compound was identified by analysis to be $\eta^5$C$_5$H$_4$(SiMe$_3$)VCl$_3$.

Elementary Analysis for C$_8$H$_{13}$Cl$_3$SiV: Calcd. (%): C, 32.62; H, 4.45; Cl 36.10; Found (%): C, 32.83; H, 4.61; Cl, 36.20.

EXAMPLE 36
Preparation of Transition Metal Compound ($\eta^5$C$_5$H$_3$(1,3-Me$_2$)VCl$_3$)

In 110 ml of THF was dissolved 10 g (110 mmol) of C$_5$H$_4$(1,3-Me$_2$) in a nitrogen stream, and the solution was cooled to −78° C. To the solution was added dropwise 80 ml (130 mmol) of a 1.61M hexane solution of n-BuLi. The reaction mixture was concentrated, and the residue was washed with hexane. The solid was dissolved in 40 ml of THF, and the solution was added dropwise to 20 ml of a toluene solution containing 2.2 ml (20 mmol) of VCl$_4$ at a THF refluxing temperature, followed by stirring at room temperature for 10 hours. The solvent was removed, and 100 ml of toluene was added to the residue. After stirring, LiCl was removed by filtration. The filtrate was concentrated to dryness to separate a green solid. The solid was dissolved in 20 ml of methylene chloride, 10 ml of toluene. was added thereto, and the system was cooled to −78° C. for crystallization. The thus formed green crystals were collected, and 50 ml of thionyl chloride was added to the residue, followed by stirring at room temperature for 10 hours. After the reaction, thionyl chloride was removed by evaporation under reduced pressure. To the residue was added 100 ml of toluene, followed by filtration. The filtrate was concentrated, 50 ml of hexane was added thereto, and deep purple crystals were obtained at −78° C. The crystals were collected by filtration and dried at room temperature under reduced pressure. The resulting compound was identified by analysis to be $\eta^5$C$_5$H$_3$(1,3-Me$_2$)VCl$_3$.

Elementary Analysis for C$_7$H$_9$Cl$_3$V: Calcd. (%): C, 33.57; H, 3.62; Cl, 42.47; Found (%): C, 33.61; H, 3.61; Cl, 42.80.

EXAMPLE 37
Preparation of Transition Metal Compound ($\eta^5$C$_5$H$_4$(t-Bu)VCl$_3$)

In 80 ml of THF was dissolved 10 g (82 mmol) of C$_5$H$_5$(t-Bu) in a nitrogen stream, and the solution was cooled to −78° C. To the solution was added dropwise 61 ml (98 mmol) of a 1.61M hexane solution of n-BuLi. The reaction mixture was concentrated, and the residue was washed with hexane. The solid was dissolved in 60 ml of THF, and the solution was added dropwise to 20 ml of a toluene solution containing 2.4 ml (23 mmol) of VCl$_4$ at a THF refluxing temperature, followed by stirring at room temperature for 10 hours. The solvent was removed, and 100 ml of methylene chloride was added to the residue, followed by stirring. LiCl was removed by filtration, and the filtrate was concentrated to dryness. Recrystallization of the solid from hexane gave deep blue crystals. To the crystals was added 50 ml of thionyl chloride, followed by stirring at room temperature for 10 hours. After the reaction, thionyl chloride was removed by evaporation under reduced pressure. To the residue was added 100 ml of toluene, followed by filtration. The filtrate was concentrated, 50 ml of hexane was added thereto, and deep purple crystals were obtained at −78° C. The crystals were collected by filtration and dried at room temperature under reduced pressure. The resulting compound was identified by analysis to be $\eta^5$C$_5$H$_4$(t-Bu)VCl$_3$.

Elementary Analysis for C$_9$H$_{13}$Cl$_3$V: Calcd. (%): C, 38.81; H, 4.72; Cl, 38.19; Found (%): C, 38.89; H, 4.89; Cl, 38.50.

EXAMPLE 38
Preparation of Transition Metal Compound ($\eta^5$C$_5$H$_4$(CH$_2$Ph)VCl$_3$)

In 20 ml of THF was dissolved 2.6 g (17 mmol) of C$_5$H$_5$(CH$_2$Ph) in a nitrogen stream, and the solution was cooled to −78° C. To the solution was added dropwise 10.4 ml (17 mmol) of a 1.60M hexane solution of n-BuLi. The reaction mixture was concentrated, and the residue was washed with hexane. The solid was dissolved in 40 ml of THF, and the solution was added dropwise to 20 ml of a toluene solution containing 0.8 ml (8 mmol) of VCl$_4$ at a THF refluxing temperature, followed by stirring at room temperature for 10 hours. The solvent was removed, and 100 ml of methylene chloride was added to the residue. After stirring, LiCl was removed by filtration. The filtrate was concentrated to dryness to obtain a green solid, and 50 ml of thionyl chloride was added thereto, followed by stirring at room temperature for 10 hours. After the reaction, thionyl chloride was removed by evaporation under reduced pressure. To the residue was added 100 ml of toluene, followed by filtration. The filtrate was concentrated, 50 ml of hexane was added thereto, and deep purple crystals were obtained at −78° C. The crystals were collected by filtration and dried at room temperature under reduced pressure. The resulting compound was identified by analysis to be $\eta^5$C$_5$H$_4$(CH$_2$Ph)VCl$_3$.

Elementary Analysis for C$_{12}$H$_{11}$Cl$_3$V: Calcd. (%): C, 46.12; H, 3.55; Cl, 34.03; Found (%): C, 46.53; H, 3.61; Cl, 34.30.

EXAMPLE 39
Preparation of Transition Metal Compound ($\eta^5C_5H_3(SiMe_3)_2VC_3$)

In 20 ml of THF was dissolved 2.1 g (10 mmol) of $C_5H_4(SiMe_3)_2$ in a nitrogen stream, and the solution was cooled to −78° C. To the solution was added dropwise 6.2 ml (10 mmol) of a 1.61M hexane solution of n-BuLi. The reaction mixture was concentrated, and the residue was washed with hexane. The solid was dissolved in 20 ml of THF, and the solution was added dropwise to 20 ml of a toluene solution containing 0.5 ml (5 mmol) of $VCl_4$ at a THF refluxing temperature, followed by stirring at room temperature for 10 hours. The solvent was removed, and 50 ml of toluene was added to the residue. After stirring, LiCl was removed by filtration. The filtrate was concentrated, and an equivalent amount of hexane was added thereto, followed by cooling to −78° C. The thus precipitated deep blue crystals were separated by filtration. To the crystals was added 15 ml of thionyl chloride, followed by stirring at room temperature for 10 hours. After the reaction, thionyl chloride was removed by evaporation under reduced pressure. To the residue was added 50 ml of toluene, followed by filtration. The filtrate was concentrated to dryness and recrystallized from hexane to obtain purple crystals. The crystals were collected by filtration and dried at room temperature under reduced pressure. The resulting compound was identified by analysis to be $\eta^5C_5H_3(SiMe_3)_2VCl_3$.

Elementary Analysis for $C_{11}H_{21}Cl_3Si_2V$: Calcd. (%): C, 36.02; H, 5.77; Cl, 29.00; Found (%): C, 36.83; H, 5.91; Cl, 29.50.

Examples 40 to 44 relates to preparation of $RM(O)X_2$ having a substituent.

EXAMPLE 40
Preparation of Transition Metal Compound ($\eta^5C_5H_4(SiMe_3)V(O)Cl_2$)

Deep blue trimethylsilylcyclopentadienyloxovanadium dichloride ($\eta^5C_5H_4(SiMe_3)V(O)Cl_2$) was synthesized by oxygen treatment of $\eta^5C_5H_4(SiMe_3)VCl_3$ prepared in Example 35 in accordance with *Organometallic*, Vol. 7, pp. 496–502 (1988).

Elementary Analysis for $C_8H_{13}Cl_2OSiV$: Calcd. (%): C, 34.93; H, 4.76; Cl, 25.77; Found (%): C, 34.73; H, 4.61; Cl, 25.61; $^1$H-NMR (CDCl$_3$): 7.01–7.00 (2H, d, Cp-H), 6.90–6.89 (2H, d, Cp-H), 0.38 (9H, s, Me$_3$Si).

EXAMPLE 41
Preparation of Transition Metal Compound

Deep blue 1,3-dimethylcyclopentadienyloxovanadium dichloride ($\eta^5C_5H_3(1,3-Me_2)V(O)Cl_2$) was synthesized by oxygen treatment of $\eta^5C_5H_3(1,3-Me_2)VCl_3$ prepared in Example 36 in accordance with *Organometallics*, Vol. 7, pp. 496–502 (1988).

Elementary Analysis for $C_7H_9Cl_2OV$: Calcd. (%): C, 36.40; H, 3.93; Cl, 30.70; Found (%): C, 36.23; H, 3.71; Cl, 30.61; $^1$H-NMR (CDCl$_3$): 6.41–6.40 (2H, d, Cp-H), 6.22 (1H, s, Cp-H), 2.52 (6H, s, Me-Cp).

EXAMPLE 42
Preparation of Transition Metal Compound

Deep blue t-butylcyclopentadienyloxovanadium dichloride ($\eta^5C_5H_4(t-Bu)V(O)Cl_2$) was synthesized by oxygen treatment of $\eta^5C_5H_4(t-Bu)VCl_3$ prepared in Example 37 in accordance with *Organometallics*, Vol. 7, pp. 496–502 (1988).

Elementary Analysis for $C_9H_{13}Cl_2OV$: Calcd. (%): C, 41.73; H, 5.06; Cl, 27.37; Found (%): C, 41.53; H, 4.91; Cl, 27.21; $^1$H-NMR (CDCl$_3$): 6.79–6.78 (2H, d, Cp-H), 6.73–6.72 (2H, d, Cp-H), 1.43 (9H, S, Me$_3$C).

EXAMPLE 43
Preparation of Transition Metal

Deep blue benzylcyclopentadienyloxovanadium dichloride ($\eta^5C_5H_4(CH_2Ph)V(O)Cl_2$) was synthesized by oxygen treatment of $\eta^5C_5H_4(CH_2Ph)VCl_3$ prepared in Example 38 in accordance with *Organometallics*, Vol. 7, pp. 496–502 (1988).

Elementary Analysis for $C_{12}H_{11}Cl_2OV$: Calcd. (%): C, 49.18; H, 3.78; Cl, 24.19; Found (%): C, 49.01; H, 3.70; Cl, 24.11; $^1$H-NMR (CDCl$_3$): 7.37–7.23 (5H, m, Ph), 6.80–6.70 (2H, d, Cp-H), 6.46–6.40 (2H, d, Cp-H), 4.20 (2H, s, CH$_2$).

EXAMPLE 44
Preparation of Transition Metal Compound

Bis(trimethylsilyl)cyclopentadienyloxovanadium dichloride ($\eta^5C_5H_3(SiMe_3)_2V(O)Cl_2$) was synthesized by oxygen treatment of $\eta^5C_5H_3(SiMe_3)_2VCl_3$ prepared in Example 39 in accordance with *Organometallics*, Vol. 7, pp. 496–502 (1988).

Elementary Analysis for $C_{11}H_{21}Cl_2OSi_2V$: Calcd. (%): C, 38.04; H, 6.09; Cl, 20.42; Found (%): C, 37.89; H, 5.97; Cl, 20.06; $^1$H-NMR (CDCl$_3$): 7.24–7.23 (2H, d, Cp-H), 6.87–6.85 (2H, t, Cp-H), 0.42 (18H, s, Si-Me).

Examples 45 to 60 offer examples of polymerization using $RMX_3$ having a substituent.

EXAMPLES 45 TO 53

Butadiene was polymerized by using (A) a substituted cyclopentadienylvanadium trichloride shown in Table 9 below, (B) triphenylcarbonium tetrakis(pentafluorophenyl)borate, and (C) triisobutylaluminum under the reaction conditions shown in Table 13. The reaction results are shown in Table 14 below.

EXAMPLES 54 TO 60

Butadiene was polymerized by using (A) a substituted cyclopentadienylvanadium trichloride shown in Table 15 and (B) MMAO under the reaction conditions shown in Table 15. The reaction results are shown in Table 16.

TABLE 13

| Example No. | Transition Metal Compound Kind | Amount (mmol) | Ph$_3$CB(C$_6$F$_5$)$_4$ (mmol) | Al(i-Bu)$_3$ (mmol) | Reaction Temp. (° C.) | Reaction Time (min) |
| --- | --- | --- | --- | --- | --- | --- |
| 45 | (MeCp)VCl$_3$ | 0.0012 | 0.0018 | 0.2 | 30 | 30 |
| 46 | (1,3-Me$_2$Cp)VCl$_3$ | 0.001 | 0.0015 | 0.2 | 30 | 30 |
| 47 | (1,3-Me$_2$Cp)VCl$_3$ | 0.002 | 0.003 | 0.2 | 30 | 30 |

TABLE 13-continued

| Example No. | Transition Metal Compound Kind | Amount (mmol) | Ph₃CB(C₆F₅)₄ (mmol) | Al(i-Bu)₃ (mmol) | Reaction Temp. (° C.) | Reaction Time (min) |
|---|---|---|---|---|---|---|
| 48 | (Me₅Cp)VCl₃ | 0.005 | 0.0075 | 0.5 | 30 | 30 |
| 49 | (Me₃SiCp)VCl₃ | 0.001 | 0.0015 | 0.2 | 30 | 30 |
| 50 | (Me₃SiCp)VCl₃ | 0.0012 | 0.0018 | 0.2 | 30 | 30 |
| 51 | (t-BuCp)VCl₃ | 0.001 | 0.0015 | 0.2 | 30 | 30 |
| 52 | (t-BuCp)VCl₃ | 0.0012 | 0.0018 | 0.2 | 30 | 30 |
| 53 | (PhCH₂Cp)VCl₃ | 0.0012 | 0.0018 | 0.2 | 30 | 30 |

TABLE 14

| Example No. | Catalytic Activity (g/mmol-V.hr) | Microstructure (%) | | | Mw (×10⁶) | Mw/Mn |
|---|---|---|---|---|---|---|
| | | cis | trans | vinyl | | |
| 45 | 5412 | 83.4 | 2.4 | 14.2 | 1.60 | 2.66 |
| 46 | 360 | 74.2 | 4.2 | 21.1 | 0.37 | 3.90 |
| 47 | 1546 | 75.1 | 4.4 | 20.5 | 0.45 | 3.20 |
| 48 | 87 | 53.8 | 7.0 | 39.2 | 0.20 | 2.00 |
| 49 | 214 | 89.7 | 3.0 | 9.8 | 0.23 | 2.11 |
| 50 | 178 | 86.0 | 4.0 | 10.0 | 0.27 | 2.04 |
| 51 | 1230 | 86.2 | 3.3 | 10.5 | 0.21 | 1.92 |
| 52 | 113 | 83.0 | 6.5 | 10.5 | 0.28 | 2.04 |
| 53 | 15387 | 85.6 | 1.7 | 12.7 | 1.72 | 2.69 |

TABLE 15

| Example No. | Transition Metal Compound Kind | Amount (mmol) | MMAO (mmol) | Reaction Temp. (° C.) | Reaction Time (min) |
|---|---|---|---|---|---|
| 54 | (MeCp)VCl₃ | 0.001 | 5 | 30 | 30 |
| 55 | (1,3-Me₂Cp)VCl₃ | 0.001 | 5 | 30 | 30 |
| 56 | (Me₅Cp)VCl₃ | 0.005 | 5 | 30 | 30 |
| 57 | (Me₃SiCp)VCl₃ | 0.001 | 5 | 30 | 30 |
| 58 | [(Me₃Si)₂Cp]VCl₃ | 0.001 | 5 | 30 | 30 |
| 59 | (t-BuCp)VCl₃ | 0.001 | 5 | 30 | 30 |
| 60 | (PhCH₂Cp)VCl₃ | 0.001 | 5 | 30 | 30 |

TABLE 16

| Example No. | Catalytic Activity (g/mmol-V.hr) | Microstructure (%) | | | Mw (×10⁶) | Mw/Mn |
|---|---|---|---|---|---|---|
| | | cis | trans | vinyl | | |
| 54 | 5188 | 85.5 | 1.8 | 12.7 | 1.73 | 2.22 |
| 55 | 2264 | 76.7 | 3.7 | 19.6 | 0.78 | 2.08 |
| 56 | 42 | 52.9 | 6.9 | 40.2 | 0.24 | 2.14 |
| 57 | 1422 | 89.7 | 1.7 | 8.6 | 1.33 | 2.58 |
| 58 | 1440 | 88.1 | 1.9 | 10.0 | 1.17 | 2.11 |
| 59 | 420 | 86.4 | 2.1 | 11.5 | 0.66 | 2.76 |
| 60 | 4264 | 86.6 | 1.3 | 12.1 | 1.46 | 2.26 |

Examples 61 to 65 furnish examples of polymerization using RM(O)X₂ compounds having a substituent.

EXAMPLES 61 TO 65

Butadiene was polymerized by using (A) a substituted cyclopentadienyloxovanadium dichloride shown in Table 17 and (B) MMAO under the reaction conditions shown in Table 17. The reaction results are shown in Table 18.

TABLE 17

| Example No. | Transition Metal Compound Kind | Amount (mmol) | MMAO (mmol) | Reaction Temp. (° C.) | Reaction Time (min) |
|---|---|---|---|---|---|
| 61 | (MeCp)V(O)Cl₂ | 0.001 | 5 | 30 | 60 |
| 62 | (1,3-Me₂Cp)V(O)Cl₂ | 0.001 | 5 | 30 | 30 |
| 63 | (Me₅Cp)V(O)Cl₂ | 0.005 | 5 | 30 | 60 |
| 64 | (Me₃SiCp)V(O)Cl₂ | 0.001 | 5 | 30 | 30 |
| 65 | (t-BuCp)V(O)Cl₂ | 0.001 | 5 | 30 | 30 |

TABLE 18

| Example No. | Catalytic Activity (g/mmol-V.hr) | Microstructure (%) | | | Mw (×10⁶) | Mw/Mn |
|---|---|---|---|---|---|---|
| | | cis | trans | vinyl | | |
| 61 | 4482 | 82.5 | 1.7 | 15.8 | 1.95 | 2.22 |
| 62 | 1190 | 77.8 | 3.1 | 19.1 | 0.78 | 2.35 |
| 63 | 68 | 52.5 | 6.6 | 40.9 | 0.25 | 2.08 |
| 64 | 2742 | 86.7 | 1.2 | 12.1 | 1.83 | 2.37 |
| 65 | 2322 | 84.6 | 1.1 | 14.3 | 1.53 | 2.22 |

Examples 66 to 77 and Comparative Example 7 relate to of using an $R_nMX_p \cdot L_a$ compound.

EXAMPLE 66

Preparation of Transition Metal Compound $(\eta^5 CH_3-C_5H_4)VCl_2[P(CH_2CH_3)_3]_2$ was synthesized in accordance with the process of *Journal of Organometallic Chemistry*, Vol. 255, p. 193 (1983) in the form of a toluene solution.

EXAMPLE 67

Preparation of Transition Metal Compound $(\eta^5 C_5H_5)_2VCl$ was synthesized in accordance with the process of *Journal of Organometallic Chemistry*, Vol. 110, p. 291 (1976) and prepared as a toluene solution.

EXAMPLE 68

Polymerization of Butadiene

To 200 ml of toluene was added a toluene solution containing 0.2 mmol of triisobutylaluminum as component (C), and the solution was kept at 40° C. To the solution was added 32 ml of butadiene, and 1.5 μmol of $(CH_3)_2NH(C_6H_5)B(C_6F_5)_4$ as component (B) and a toluene solution of 1.0 μmol of the transition metal compound prepared in Example 66 as component (A) were added thereto. Polymerization was carried out for 1 hour. The reaction was stopped by addition of an HCl-containing ethanol solution, and the reaction mixture was filtered. The filter cake was dried to obtain a white butadiene polymer. The reaction results are shown in Table 20 below.

EXAMPLES 69 TO 71
Polymerization of Butadiene

Butadiene was polymerized in the same manner as in Example 68, except for changing the reaction conditions as shown in Table 19 below. The reaction results are shown in Table 20.

EXAMPLES 72 TO 73
Polymerization of Butadiene

Butadiene was polymerized in the same manner as in Example 68, except for using the transition metal compound prepared in Example 67 as component (A) and changing the reaction conditions as shown in Table 19. The reaction results are shown in Table 20.

EXAMPLES 74 TO 76
Polymerization of Butadiene

Butadiene was polymerized in the same manner as in Example 68, except for using the transition metal compound prepared in Example 66 as component (A) and $Ph_3CB(C_6F_5)_4$ as component (B) and changing the reaction conditions as shown in Table 19. The reaction results are shown in Table 20.

EXAMPLE 77
Polymerization of Butadiene

To 200 ml of toluene was added a toluene solution containing 0.2 mmol of triisobutylaluminum, and the solution was maintained at 10° C. To the solution was added 0.5 ml of butadiene, and 1.5 μmol of $(CH_3)_2NH(C_6H_5)B(C_6F_5)_4$ and a toluene solution of 1.0 μmol of the transition metal compound prepared in Example 60 were then added, followed by stirring for 2 hours. The solution was maintained at 40° C., and 32 ml of butadiene was added thereto to commence reaction. Polymerization reaction was continued for 1 hour. The reaction was stopped by addition of an HCl-containing ethanol solution, and the reaction mixture was filtered. The filter cake was dried to obtain a white butadiene polymer. The reaction results are shown in Table 20 below.

COMPARATIVE EXAMPLE 7
Polymerization of Butadiene

Butadiene was polymerized in the same manner as in Example 68, except for using 1.0 μmol of the transition metal compound prepared in Example 66 and 0.2 mmol of methylaluminoxane as catalyst components. The reaction results are shown in Table 20.

TABLE 19

| Example No. | Component (A) (μmol) | Component (B) (μmol) | Component (C) (mmol) | $H_2$ (ml/min) |
|---|---|---|---|---|
| 68 | 1 | 1.5 | 0.2 | — |
| 69 | 1 | 1.5 | 1.0 | — |
| 70 | 1 | 1.5 | 0.2 | 20 |
| 71 | 1 | 1.5 | 0.2 | 10 |
| 72 | 1 | 1.5 | 0.2 | — |
| 73 | 1 | 1.5 | 0.2 | 10 |
| 74 | 1 | 1.5 | 0.2 | — |
| 75 | 1 | 1.5 | 0.2 | 20 |
| 76 | 1 | 1.5 | 0.2 | 10 |
| 77 | 1 | 1.5 | 0.2 | — |

TABLE 20

| Example No. | Catalytic Activity (g/mmol-V.hr) | Microstructure (%) | | | Mw ($\times 10^4$) | Mw/Mn |
|---|---|---|---|---|---|---|
| | | cis | trans | vinyl | | |
| 68 | 1400 | 84.5 | 1.3 | 14.2 | 242.0 | 2.3 |
| 69 | 1600 | 84.2 | 1.0 | 14.8 | 224.4 | 2.3 |
| 70 | 1200 | 83.0 | 2.9 | 14.1 | 1.9 | 1.8 |
| 71 | 900 | 82.6 | 3.1 | 14.3 | 8.9 | 2.0 |
| 72 | 500 | 84.3 | 1.5 | 14.2 | 212.3 | 2.4 |
| 73 | 400 | 84.0 | 2.8 | 13.2 | 15.6 | 2.5 |
| 74 | 1300 | 82.1 | 2.1 | 15.8 | 236.0 | 2.2 |
| 75 | 800 | 82.5 | 2.4 | 15.1 | 2.3 | 1.8 |
| 76 | 700 | 81.9 | 2.6 | 15.5 | 21.0 | 2.1 |
| 77 | 800 | 82.1 | 2.1 | 15.8 | 216.1 | 2.2 |
| Comparative Example 7 | 400 | 81.4 | 1.3 | 17.3 | 192.2 | 2.3 |

Examples 78 to 89 and Comparative Examples 8 to 12 relate to polymerization in the presence of hydrogen.

EXAMPLES 78 TO 80

To a 1.5 l autoclave having been purged with nitrogen were charged 300 ml of toluene and 62 g of 1,3-butadiene, and the mixture was stirred. A pressure container having a capacity corresponding to the amount of hydrogen shown in Table 21 below was filled with hydrogen at 20° C. and atmospheric pressure, and hydrogen was introduced into the autoclave with nitrogen pressure. To the autoclave were then fed 2 ml of a toluene solution containing 5 mmol of an aluminoxane prepared from a mixture of trimethylaluminum and tributylaluminum (MMAO, produced by Tosoh-Akzo Corp.) and 0.01 mmol of cyclopentadienylvanadium trichloride ($CpVCl_3$), and polymerization was carried out at 40° C. for 60 minutes.

After the reaction, ethanol containing a small amount of 2,6-di-t-butyl-p-cresol was added to the reaction system, and the thus precipitated polymer was collected by filtration and dried. The reaction results are shown in Table 22 below.

EXAMPLES 81 TO 84

To a 1.5 l autoclave having been purged with nitrogen were charged 300 ml of toluene and 62 g of 1,3-butadiene, and the mixture was stirred. A pressure container having a capacity corresponding to the amount of hydrogen shown in Table 23 below was filled with hydrogen at 20° C. and atmospheric pressure, and hydrogen was introduced into the autoclave with nitrogen pressure. To the autoclave were then fed 0.5 ml of a toluene solution containing 0.5 mmol of triisobutylaluminum, 1.5 ml of a toluene solution containing 0.0075 mmol of triphenylcarbonium tetrakis (pentafluorophenyl)borate ($Ph_3CB(C_6F_5)_4$), and 0.1 ml of a toluene solution containing 0.005 mmol of cyclopentadienylvanadium trichloride ($CpVCl_3$), and polymerization was carried out at 40° C. for 20 minutes.

After the reaction, ethanol containing a small amount of 2,6-di-t-butyl-p-cresol was added to the reaction system, and the thus precipitated polymer was collected by filtration and dried. The reaction results are shown in Table 24 below.

EXAMPLES 85 TO 89

To a 1.5 l autoclave having been purged with nitrogen were charged 300 ml of cyclohexane and 62 g of 1,3-butadiene, and the mixture was stirred. A pressure container having a capacity corresponding to the amount of hydrogen shown in Table 25 below was filled with hydrogen at 20° C. and atmospheric pressure, and hydrogen was introduced into the autoclave with nitrogen pressure. To the autoclave were then fed 0.25 ml of a toluene solution containing 0.25 mmol of triethylaluminum, 2 ml of a toluene solution containing 0.01 mmol of triphenylcarbonium tetrakis (pentafluorophenyl)borate (Ph$_3$CB(C$_6$F$_5$)$_4$), and 0.1 ml of a toluene solution containing 0.005 mmol of cyclopentadienylvanadium trichloride (CpVCl$_3$), and polymerization was carried out at 40° C. for 60 minutes.

After the reaction, ethanol containing a small amount of 2,6-di-t-butyl-p-cresol was added to the reaction system, and the thus precipitated polymer was collected by filtration and dried. The reaction results are shown in Table 26 below.

COMPARATIVE EXAMPLE 8 TO 10

Butadiene was polymerized in the same manner as in Example 85, except for replacing hydrogen gas with a toluene solution of 1,5-cyclooctadiene, the amount of which is shown in Table 27 below, which was fed by means of a syringe. The n results are shown in Table 28.

COMPARATIVE EXAMPLE 11 TO 12

Butadiene was polymerized in the same manner as in Example 85, except for replacing hydrogen gas with a toluene solution of 1,2-butadiene, the amount of which is shown in Table 29 below, which was fed by means of a syringe. The reaction results are shown in Table 30.

TABLE 21

| Example No. | Hydrogen Gas (20° C., 1 atm) (ml) | Yield (g) | Catalytic Activity (g/mmol-V.hr) |
|---|---|---|---|
| 78 | 30 | 34.4 | 3440 |
| 79 | 50 | 35.0 | 3500 |
| 80 | 78 | 32.0 | 3200 |

TABLE 22

| Example No. | Microstructure (%) | | | [η] | Mw (×10$^6$) | Mw/Mn |
|---|---|---|---|---|---|---|
| | cis | trans | vinyl | | | |
| 78 | 89.6 | 1.4 | 9.0 | 3.90 | 1.20 | 2.50 |
| 79 | 89.5 | 1.3 | 9.2 | 2.21 | 0.60 | 2.40 |
| 80 | 90.1 | 1.2 | 8.7 | 1.50 | 0.31 | 2.07 |

TABLE 23

| Example No. | Hydrogen Gas (20° C., 1 atm) (ml) | Yield (g) | Catalytic Activity (g/mmol-V.hr) |
|---|---|---|---|
| 81 | 10 | 36.0 | 21600 |
| 82 | 30 | 41.0 | 24600 |
| 83 | 50 | 39.2 | 23520 |
| 84 | 78 | 35.2 | 21120 |

TABLE 24

| Example No. | Microstructure (%) | | | [η] | Mw (×10$^6$) | Mw/Mn |
|---|---|---|---|---|---|---|
| | cis | trans | vinyl | | | |
| 81 | 88.3 | 2.0 | 9.7 | 6.50 | 1.55 | 2.21 |
| 82 | 88.3 | 1.7 | 10.0 | 3.51 | 0.96 | 2.18 |
| 83 | 87.4 | 1.9 | 10.7 | 2.02 | 0.46 | 2.30 |
| 84 | 88.4 | 1.8 | 9.8 | 1.30 | 0.27 | 1.93 |

TABLE 25

| Example No. | Hydrogen Gas (20° C., 1 atm) (ml) | Yield (g) | Catalytic Activity (g/mmol-V.hr) |
|---|---|---|---|
| 85 | 10 | 34.4 | 6880 |
| 86 | 30 | 39.2 | 7840 |
| 87 | 50 | 35.0 | 7000 |
| 88 | 78 | 38.2 | 7640 |
| 89 | 120 | 37.0 | 7400 |

TABLE 26

| Example No. | Microstructure (%) | | | [η] | Mw (×10$^6$) | Mw/Mn |
|---|---|---|---|---|---|---|
| | cis | trans | vinyl | | | |
| 85 | 87.3 | 1.2 | 11.5 | 5.86 | 1.48 | 2.10 |
| 86 | 87.4 | 1.5 | 11.1 | 2.60 | 0.68 | 2.27 |
| 87 | 87.3 | 1.4 | 11.3 | 1.67 | 0.34 | 2.05 |
| 88 | 87.3 | 1.4 | 11.3 | 1.24 | 0.22 | 2.06 |
| 89 | 87.3 | 1.4 | 11.3 | 0.81 | 0.12 | 1.89 |

TABLE 27

| Comparative Example No. | 1,5-Cyclo-octadiene (mmol) | Yield (g) | Catalytic Activity (g/mmol-V.hr) |
|---|---|---|---|
| 8 | 3 | 43.6 | 8720 |
| 9 | 6 | 44.0 | 8800 |
| 10 | 10 | 4.7 | 940 |

TABLE 28

| Comparative Example No. | Microstructure (%) | | | [η] | Mw (×10$^6$) | Mw/Mn |
|---|---|---|---|---|---|---|
| | cis | trans | vinyl | | | |
| 8 | 86.8 | 1.0 | 12.2 | 8.82 | 2.04 | 2.13 |
| 9 | 86.9 | 1.3 | 11.8 | 8.01 | 1.82 | 1.83 |
| 10 | 86.8 | 1.2 | 12.0 | 5.24 | 1.30 | 2.67 |

TABLE 29

| Comparative Example No. | 1,2-Butadiene (mmol) | Yield (g) | Catalytic Activity (g/mmol-V.hr) |
|---|---|---|---|
| 11 | 0.3 | 10.6 | 2120 |
| 12 | 3.0 | 0 | — |

TABLE 30

| Comparative Example No. | Microstructure (%) | | | [η] | Mw (×10$^6$) | Mw/Mn |
|---|---|---|---|---|---|---|
| | cis | trans | vinyl | | | |
| 11 | 87.0 | 1.0 | 12.0 | 9.50 | 2.11 | 2.32 |
| 12 | — | — | — | — | — | — |

EXAMPLE 90

To 200 ml of toluene was added 0.2 mmol of triisobutylaluminum as a toluene solution, and the resulting solution was maintained at 40° C. To the solution was added 33 ml of butadiene, and then added 1.5 μmol of $(CH_3)_2NH(C_6H_5)$ $B(C_6F_5)_4$. Polymerization was carried out for 1 hour by adding 1.0 μmol of cyclopentadienyloxovanadium dichloride as a toluene solution, while hydrogen was added at a rate of 5 ml/min. Polmerization was terminated by adding an HCl-containing ethanol solution to the reaction system, and the thus precipitated polymer was collected by filtration and dried to obtain white polybutadiene. The catalyst activity was 8100 g/mmol-V.hr. The microstructure of the polybutadiene was that cis was 87.2%, trans was 3.6%, and vinyl was 9.2%. Mw was $0.502 \times 10^6$ and Mw/Mn was 1.59.

EXAMPLE 91

Butadiene was polymerized in the same manner as in Example 90, except for changing the addition rate of hydrogen to 20 ml/min. Polmerization was terminated by adding an HCl-containing ethanol solution to the reaction system, and the thus precipitated polymer was collected by filtration and dried to obtain white polybutadiene. The catalyst activity was 5200 g/mmol-V.hr. The microstructure of the polybutadiene was that cis was 86.7%, trans was 5.9%, and vinyl was 7.4%. Mw was $0.091 \times 10^6$ and Mw/Mn was 2.86.

Examples 92 to 108 provide examples of bulk polymerization.

EXAMPLE 92

To a 1.7 l autoclave having been purged with nitrogen was charged 248 g (400 ml) of 1,3-butadiene, and 5 mmol of aluminoxane prepared from a mixture of trimethylaluminum and tributylaluminum (MMAO, produced by Tosoh-Akzo Corp.) and 0.005 mmol of cyclopentadienylvanadium trichloride ($CpVCl_3$) were added thereto. Polymerization was carried out at 40° C. for 60 minutes.

After the reaction, ethanol containing a small amount of 2,6-di-t-butyl-p-cresol was added to the reaction system, and the thus precipitated polymer was collected by filtration and dried. The reaction results are shown in Table 32 below.

EXAMPLES 93 TO 94

Butadiene was polymerized in the same manner as in Example 92, except for changing the reaction conditions as shown in Table 31 below. The reaction results are shown in Table 32.

EXAMPLE 95

To a 1.7 l autoclave having been purged with nitrogen was charged 248 g (400 ml) of 1,3-butadiene, and 0.5 mmol of triethylaluminum, 0.01 mmol of triphenylcarbonium tetrakis (pentafluorophenyl)borate $(Ph_3CB(C_6F_5)_4)$, and 0.005 mmol of cyclopentadienylvanadium trichloride ($CpVCl_3$) were added thereto. Polymerization was carried out at 40° C. for 15 minutes.

After the reaction, ethanol containing a small amount of 2,6-di-t-butyl-p-cresol was added to the reaction system, and the thus precipitated polymer was collected by filtration and dried. The reaction results are shown in Table 34 below.

EXAMPLES 96 TO 100

Butadiene was polymerized in the same manner as in Example 92, except for performing the polymerization in the presence of hydrogen as shown in Table 33 and changing the reaction conditions as shown in Table 33. The reaction results are shown in Table 34.

EXAMPLE 101

To a 1.7 l autoclave having been purged with nitrogen was charged 248 g (400 ml) of 1,3-butadiene, and hydrogen gas of the amount shown in Table 31 below was introduced into the autoclave. Then, 0.5 mmol of triethylaluminum, 0.005 mmol of cyclopentadienylvanadium trichloride ($CpVCl_3$), and 0.01 mmol of triphenylcarbonium tetrakis (pentafluorophenyl)borate $(Ph_3CB(C_6F_5)_4)$ were added thereto. Polymerization was carried out at 40° C. for 15 minutes.

After the reaction, ethanol containing a small amount of 2,6-di-t-butyl-p-cresol was added to the reaction system, and the thus precipitated polymer was collected by filtration The reaction results are shown in Table 36 below.

EXAMPLES 102 TO 103

Butadiene was polymerized in the same manner as in Example 101, except for changing the reaction conditions as shown in Table 35. The reaction results are shown in Table 36.

TABLE 31

| Example No. | $CpVCl_3$ (mmol) | MMAO (mmol) | Reaction Temp. (° C.) | Reaction Time (min) |
|---|---|---|---|---|
| 92 | 0.005 | 5 | 40 | 60 |
| 93 | 0.005 | 15 | 40 | 15 |
| 94 | 0.005 | 25 | 40 | 15 |

TABLE 32

| Example No. | Yield (g) | Catalytic Activity (g/mmol-V.hr) | Microstructure (%) | | | Mw ($\times 10^6$) | Mn ($\times 10^6$) | Mw/Mn |
|---|---|---|---|---|---|---|---|---|
| | | | cis | trans | vinyl | | | |
| 92 | 28.0 | 5600 | 89.9 | 0.8 | 9.3 | 2.93 | 1.24 | 2.36 |
| 93 | 39.5 | 31600 | 89.9 | 0.7 | 9.4 | 3.08 | 1.58 | 1.95 |
| 94 | 49.6 | 39680 | 90.1 | 0.6 | 9.3 | 3.10 | 1.53 | 2.03 |

TABLE 33

| Example No. | CpVCl$_3$ (mmol) | TEA (mmol) | Ph$_3$CB-(C$_6$F$_5$)$_4$ (mmol) | H$_2$ (kgf/cm$^2$; ml) | Reaction Temp. (° C.) | Reaction Time (min) |
|---|---|---|---|---|---|---|
| 95 | 0.005 | 0.5 | 0.01 | — | 40 | 15 |
| 96 | 0.005 | 0.5 | 0.01 | 0.06; 78 | 40 | 15 |
| 97 | 0.005 | 0.5 | 0.01 | 0.1; 128 | 40 | 60 |
| 98 | 0.005 | 0.5 | 0.01 | 0.16; 208 | 40 | 15 |
| 99 | 0.005 | 0.5 | 0.01 | 0.16; 208 | 40 | 60 |
| 100 | 0.005 | 0.5 | 0.01 | 0.2; 260 | 40 | 60 |

TABLE 34

| Example No. | Yield (g) | Catalytic Activity (g/mmol-V.hr) | Microstructure (%) | | | Mw (× 10$^6$) | Mn (× 10$^6$) | Mw/Mn | [η] |
|---|---|---|---|---|---|---|---|---|---|
| | | | cis | trans | vinyl | | | | |
| 95 | 41.0 | 32800 | 87.8 | 0.8 | 11.4 | 3.41 | 1.19 | 2.85 | 17.42 |
| 96 | 66.4 | 53120 | 88.1 | 0.7 | 11.2 | 1.80 | 0.88 | 2.05 | 7.79 |
| 97 | 77.3 | 15460 | 88.0 | 0.8 | 11.2 | 1.19 | 0.54 | 2.20 | 5.45 |
| 98 | 41.3 | 33040 | 87.8 | 0.9 | 11.3 | 0.44 | 0.18 | 2.44 | 1.76 |
| 99 | 75.5 | 15100 | 87.8 | 0.9 | 11.3 | 0.40 | 0.20 | 2.02 | 1.93 |
| 100 | 58.0 | 11600 | 87.8 | 0.8 | 11.4 | 0.22 | 0.12 | 1.95 | 1.25 |

TABLE 35

| Example No. | CpVCl$_3$ (mmol) | TEA (mmol) | Ph$_3$CB-(C$_6$F$_5$)$_4$ (mmol) | H$_2$ (kgf/cm$^2$; ml) | Reaction Temp. (° C.) | Reaction Time (min) |
|---|---|---|---|---|---|---|
| 101 | 0.005 | 0.5 | 0.01 | 0.16; 208 | 40 | 15 |
| 102 | 0.005 | 0.5 | 0.01 | 0.20; 260 | 40 | 15 |
| 103 | 0.005 | 0.5 | 0.01 | 0.26; 338 | 40 | 60 |

TABLE 36

| Example No. | Yield (g) | Catalytic Activity (g/mmol-V.hr) | Microstructure (%) | | | Mw (× 10$^6$) | Mn (× 10$^6$) | Mw/Mn | [η] |
|---|---|---|---|---|---|---|---|---|---|
| | | | cis | trans | vinyl | | | | |
| 101 | 83.8 | 67040 | 87.8 | 0.9 | 11.3 | 1.52 | 0.74 | 2.05 | 6.17 |
| 102 | 82.8 | 66240 | 87.8 | 0.9 | 11.3 | 1.05 | 0.50 | 2.10 | 4.01 |
| 103 | 87.7 | 17540 | 87.8 | 0.8 | 11.4 | 0.30 | 0.13 | 2.31 | 1.40 |

EXAMPLE 104

A 1.7 l autoclave was purged with nitrogen, and 248 g (400 ml) of 1,3-butadiene was charged therein to a pressure of 0.16 Kgf/cm$^2$. To the system were added 0.75 mmol of triethylalminum and 0.01 mmol of N,N-dimethylanilinium tetrakis(pentafluorophenyl)borate, and polymerization reaction was carried out at 40° C. for 15 minutes. After completion of polymerization, etanol containing a small amount of 2,6-t-butyl-p-cresol was added to the reaction system to precipitate the polymer thus produced, and the polymer was then filtered and dried. The reaction results are shown in Tables 38 and 39.

EXAMPLES 105 TO 108

The polymerization of 1,3-butadiene was carried out in the same manner as in Example 104, except for changing the reaction conditions as shown in Table 37. The reaction results are shown in Tables 38 and 39.

TABLE 37

| Example No. | CpVCl$_3$ (mmol) | TEA (mmol) | Me$_2$PhNH B(C$_6$F$_5$)$_4$ (mmol) | H$_2$ (kgf/cm$^2$; ml) | Reaction Temp. (° C.) | Reaction Time (min) |
|---|---|---|---|---|---|---|
| 104 | 0.005 | 0.75 | 0.01 | — | 40 | 5 |
| 105 | 0.005 | 0.75 | 0.01 | 0.10; 130 | 40 | 60 |
| 106 | 0.005 | 0.75 | 0.01 | 0.15; 195 | 40 | 60 |

TABLE 37-continued

| Example No. | CpVCl$_3$ (mmol) | TEA (mmol) | Me$_2$PhNH B(C$_6$F$_5$)$_4$ (mmol) | H$_2$ (kgf/cm$^2$; ml) | Reaction Temp. (° C.) | Reaction Time (min) |
|---|---|---|---|---|---|---|
| 107 | 0.005 | 0.75 | 0.01 | 0.20; 260 | 40 | 60 |
| 108 | 0.005 | 0.75 | 0.01 | 0.30; 390 | 40 | 60 |

TABLE 38

| Example No. | Yield (g) | Catalytic Activity (g/mmol-V.hr) | Microstructure (%) | | |
|---|---|---|---|---|---|
| | | | cis | trans | vinyl |
| 104 | 96.9 | 232560 | | | |
| 105 | 77.1 | 15420 | 88.2 | 0.6 | 11.2 |
| 106 | 75.3 | 15060 | 88.4 | 0.6 | 11.0 |
| 107 | 83.9 | 16780 | 88.4 | 0.7 | 10.9 |
| 108 | 62.7 | 12540 | 88.1 | 0.9 | 11.0 |

TABLE 39

| Example No. | Mw (× 10⁶) | Mn (× 10⁶) | Mw/Mn | [η] | Gel Content (%) |
|---|---|---|---|---|---|
| 104 | | | | 19.14 | |
| 105 | 0.711 | 0.281 | 2.54 | 3.21 | 0.002 |
| 106 | 0.416 | 0.174 | 2.40 | 2.09 | 0.003 |
| 107 | 0.254 | 0.120 | 2.11 | 1.44 | 0.000 |
| 108 | 0.117 | 0.063 | 1.85 | 0.81 | 0.000 |

Examples 109 to 111 relate to production of polybutadiene having a specific B value. In these Examples, $^{13}$C-NMR spectra of polybutadiene produced were taken under the following conditions.

Equipment: FT-NMR, JEOL Model EX-400
Sample tube: 5 mm in diameter
Solvent: o-dichlorobenzene/$C_6D_6$ (4/1)
Concentration: 10%
Temperature: 130° C.
Standard: TMS
Width of observation: 20,000 Hz
Method of measurement: proton noise decoupling
Data point: 32K
Number of integration: 5000
Pulse width: 3 sec (45°)

EXAMPLE 109

Synthesis of Cyclopentadienylvanadium Trichloride

Cyclopentadienylvanadium trichloride was prepared in the same manner as in Example 1.

Polymerization of 1,3-Butadiene

A 1.5 l autoclave was purged with nitrogen, and 300 ml of toluene and 62 g of 1,3-butadiene were charged therein. To the mixture were added 2 ml of a toluene solution containing 2.5 mmol/ml-toluene of methylaluminoxane (MMAO) prepared from a mixture of trimethylaluminum and tributylaluminum and 0.2 ml of a toluene solution containing 0.05 mmol/ml-toluene of cyclopentadienylvanadium trichloride (CpVCl₃), and polymerization reaction was carried out at 40° C. for 60 minutes. After completion of polymerization, unreacted 1,3-butadiene was released from the autoclave, and an antioxidant was added to the reaction mixture. The reaction mixture was poured into ethanol, and the thus precipitated polymer was collected, washed, filtered, and dried. The reaction results are shown in Table 40 below.

The diad chain contents and the microstructure of the resulting polybutadiene were obtained from the $^{13}$C-NMR spectrum, and B value was calculated therefrom. The results obtained are shown in Table 41.

EXAMPLE 110

Polymerization of 1,3-butadiene was carried out in the same manner as in Example 9. The reaction results are shown in Table 40 below.

The diad chain contents, microstructure, and B value butadiene are shown in Table 41.

EXAMPLE 111

Polymerization of butadiene was carried out in the same manner as in Example 110, except for using 0.01 mmol of CpVCl₃, 0.01 mmol of Ph₃CB($C_6F_5$)₄, and 2 mmol of MMAO. The reaction results are shown in Table 40. The diad chain contents, microstructure, and B value of the resulting polybutadiene are shown in Table 41.

TABLE 40

| Example No. | Yield (g) | Catalytic Activity (g/mmol-V.hr) |
|---|---|---|
| 109 | 36.0 | 3600 |
| 110 | 36.8 | 22080 |
| 111 | 42.9 | 8580 |

TABLE 41

| | Example 109 | Example 110 | Example 111 |
|---|---|---|---|
| Microstructure (%): | | | |
| (cis-1,4) | 86.0 | 84.6 | 84.4 |
| (trans-1,4) | 3.2 | 4.0 | 3.6 |
| (1,2) | 10.8 | 11.4 | 12.0 |
| Diad Chain (%): | | | |
| (cis-1,4)(1,2) | 10.3 | 10.6 | 11.1 |
| (1,2)(cis-1,4) | 9.8 | 9.7 | 10.4 |
| (trans-1,4)(1,2) | 0.0 | 0.0 | 0.0 |
| (1,2)(trans-1,4) | 0.5 | 0.9 | 0.7 |
| (cis-1,4)(1,4) | 75.7 | 74.0 | 73.3 |
| (trans-1,4)(1,4) | 3.2 | 4.0 | 3.6 |
| (1,2)(1,2) | 0.5 | 0.8 | 0.9 |
| $P_{1,2}$ | 0.108 | 0.114 | 0.120 |
| $P_{1,4}$ | 0.892 | 0.886 | 0.880 |
| $P_{1,2-1,4}$ | 0.206 | 0.212 | 0.222 |
| B | 1.07 | 1.05 | 1.05 |

Examples 112 to 120 illustrate production of polybutadiene having a specific intrinsic viscosity and a specific gel content.

EXAMPLE 112

A 1.5 l autoclave was purged with nitrogen, and 300 ml of toluene and 62 g of 1,3-butadiene were charged therein. To the mixture were added a toluene solution containing 0.5 mmol of triisobutylaluminum as component (C), a toluene solution containing 0.0075 mmol of triphenylcarbonium tetrakis(pentafluorophenyl)borate (Ph₃CB($C_6F_5$)₄) as component (B), and a toluene solution containing 0.005 mmol of cyclopentadienylvanadium trichloride (CpVCl₃), and polymerization reaction was carried out at 40° C. for 20 minutes. The polymerization conditions and the reaction results are shown in Tables 42 and 43, respectively. The analytical results of the resulting polybutadiene are shown in Table 44.

EXAMPLE 113

A 1.5 l autoclave was purged with nitrogen, and 300 ml of toluene and 62 g of 1,3-butadiene were charged therein. To the mixture were added a toluene solution containing 5 mmol of methylaluminoxane (MMAO) prepared from a mixture of trimethylaluminum and tributylaluminum as component (B) and a toluene solution containing 0.01 mmol of cyclopentadienylvanadium trichloride (CpVCl₃) as component (A), and polymerization reaction was carried out at 40° C. for 60 minutes. After completion of polymerization, unreacted 1,3-butadiene was released from the autoclave, and an antioxidant was added to the reaction mixture. The reaction mixture was poured into ethanol, and the thus precipitated polymer was collected, washed, filtered, and dried. The polymerization conditions and the reaction results are shown in Tables 42 and 43, respectively. The analytical results of the resulting polybutadiene are shown in Table 44.

EXAMPLES 114 TO 116

Polymerization was carried out in the same manner as in Example 112, except for using cyclohexane as a polymerization solvent. The polymerization conditions and the reaction results are shown in Tables 42 and 43, respectively. The analytical results of the resulting polybutadiene are shown in Table 44.

EXAMPLE 117

Polymerization was carried out in the same manner as in Example 116, except for using triethylaluminum as component (C). The polymerization conditions and the reaction results are shown in Tables 42 and 43, respectively. The analytical results of the resulting polybutadiene are shown in Table 44.

EXAMPLE 118

Polymerization was carried out in the same manner as in Example 99, except for using cyclohexane as a polymerization solvent. The polymerization conditions and the reaction results are shown in Tables 42 and 43, respectively. The analytical results of the resulting polybutadiene are shown in Table 44.

EXAMPLE 119

A 1 l autoclave was purged with nitrogen, and 200 ml of toluene and a toluene solution containing 0.2 mmol of triisobutylaluminum as component (C) were charged therein. To the mixture were then added a toluene solution containing 0.0015 mmol of $((CH_3)_2NH(C_6H_5)B(C_6F_5)_4)$ as component (B) and a toluene solution containing 0.001 mmol of cyclopentadienyloxovanadium dichloride (CpV(O)Cl$_2$) as component (A). Polymerization reaction was carried out at 40° C. for 20 minutes. The polymerization conditions and the reaction results are shown in Tables 42 and 43, respectively. The analytical results of the resulting polybutadiene are shown in Table 44.

EXAMPLE 120

Polymerization was carried out in the same manner as in Example 105, except that a toluene solution containing 1 mmol of methylaluminoxane (MMAO) prepared from a mixture of trimethylaluminum and tributylaluminum was used as component (B), and component (C) was not used. The polymerization conditions and the reaction results are shown in Tables 42 and 43, respectively. The analytical results of the resulting polybutadiene are shown in Table 44.

TABLE 42

| Example No. | Component (A) (mmol) | Component (B) (mmol) | Component (C) (mmol) | Reaction Temp. (° C.) | Reaction Time (min) |
|---|---|---|---|---|---|
| 112 | 0.005 | 0.0075 | 0.5 | 40 | 20 |
| 113 | 0.01 | 5 | — | 40 | 60 |
| 114 | 0.005 | 0.0075 | 0.25 | 40 | 60 |
| 115 | 0.005 | 0.0075 | 0.5 | 40 | 60 |
| 116 | 0.005 | 0.01 | 0.25 | 40 | 60 |
| 117 | 0.005 | 0.01 | 0.25 | 40 | 60 |
| 118 | 0.01 | 5 | — | 40 | 60 |
| 119 | 0.001 | 0.0015 | 0.2 | 40 | 60 |
| 120 | 0.001 | 1 | — | 40 | 60 |

TABLE 43

| Example No. | Yield (g) | Catalytic Activity (g/mmol-V.h) |
|---|---|---|
| 112 | 36.8 | 22080 |
| 113 | 36.0 | 3600 |
| 114 | 22.4 | 4480 |
| 115 | 16.0 | 3200 |
| 116 | 28.1 | 5620 |
| 117 | 47.0 | 9400 |
| 118 | 33.9 | 3390 |
| 119 | 10.2 | 10200 |
| 120 | 6.2 | 6200 |

TABLE 44

| Example No. | Microstructure (%) | | | [η] | Mw (× 10$^6$) | Mn (× 10$^6$) | Mw/Mn | Gel Content (%) |
|---|---|---|---|---|---|---|---|---|
| | cis | trans | 1,2- | | | | | |
| 112 | 88.4 | 1.9 | 9.7 | 12.00 | 2.63 | 1.14 | 2.31 | 0.006 |
| 113 | 90.2 | 1.2 | 8.6 | 14.00 | 2.90 | 1.04 | 2.79 | 0.006 |
| 114 | 86.8 | 1.1 | 12.1 | 14.51 | 2.94 | 1.42 | 2.07 | 0.021 |
| 115 | 87.2 | 1.0 | 11.8 | 10.32 | 2.33 | 0.96 | 2.42 | 0.022 |
| 116 | 86.7 | 1.3 | 12.0 | 16.20 | 3.17 | 1.58 | 2.01 | 0.036 |
| 117 | 86.7 | 1.6 | 11.7 | 11.03 | 2.39 | 1.02 | 2.34 | 0.012 |
| 118 | 89.5 | 1.2 | 9.3 | 9.96 | 2.20 | 1.00 | 2.20 | 0.014 |
| 119 | 88.9 | 1.7 | 9.4 | 14.33 | 2.92 | 0.99 | 2.96 | 0.008 |
| 120 | 89.9 | 1.8 | 8.3 | 12.10 | 2.54 | 1.23 | 2.06 | 0.008 |

While the invention has been described in detail and with reference to specific examples thereof, it will be apparent to one skilled in the art that various changes and modifications can be made therein without departing from the spitit and scope thereof.

What is claimed is:

1. A catalyst obtained by contacting
   (A) a compound of a transition metal of the group V of the Periodic Table represented by formula (I):

$$R_nM(O)_mX_p \cdot L_a \qquad (I)$$

wherein M represents a transition metal of the group V of the periodic table: R represents a cyclopentadienyl group, a substituted cyclopentadienyl group having at least one substituent selected from the group consisting of hydrocarbon groups and silicon-containing hydrocarbon groups, an indenyl group, a substituted indenyl group having at least one substituent selected from the group consisting of hydrocarbon groups and silicon-containing hydrocarbon groups, a fluorenyl group or a substituted fluorenyl group having at least one substituent selected from the group consisting of hydrocarbon groups and silicon-containing hydrocarbon groups; O represents an oxygen atom; X represents a hydrogen atom, a halogen atom, a hydrocarbon group having 1–20 carbon atoms, an alkoxy group, an aryloxy group or an amido group; L represents a Lewis basic compound; n, m, and p each represent an integer selected to make a combination of (n=1, m=1, p=2), (n=1, m=0, p=3), (n=2, m=0, p=1) or (n=1, m=0, p=2); and a represents 0, 1 or 2, and (B) at least one of (B1) an ionic compound comprising a non-coordinating anion and a cation and (B2) an aluminoxane, provided that said component (B) is an ionic compound comprising a non-coordinating anion and a cation (B1) when the combination of n, m, and p of said component (A) is (n=2, m=0, p=1) or (n=1, m=0, p=2).

2. A catalyst as claimed in claim 1, wherein said catalyst obtained by contacting said components (A) and (B) and (C) an organic compound of the group I, II or III metal of the Periodic Table.

3. A catalyst as claimed in claim 1, wherein said compound of a transition metal of the group V of the Periodic Table represented by the formula (I) as component (A) is a compound represented by the formula $RMX_3$, wherein R, M and X have the same meanings as in claim 1.

4. A catalyst as claimed in claim 1, wherein said compound of a transition metal of the group V of the Periodic Table represented by formula (I) as component (A) is a vanadium compound.

5. A catalyst as claimed in claim 1, wherein said compound of a transition metal of the group V of the Periodic Table represented by formula (I) as component (A) is a compound represented by the formula $RMX_3$, wherein R, M and X have the same meanings as in claim 1 and said component (B) is an ionic compound comprising a non-coordinating anion and a cation (B1).

6. A catalyst comprising (A) a compound of a transition metal of the group V of the Periodic Table represented by formula (I):

(I)

wherein M represents a transition metal of the group V of the Periodic Table; R represents a cyclopentadienyl group, a substituted cyclopentadienyl group having at least one substituent selected from the group consisting of hydrocarbon groups and silicon-containing hydrocarbon groups, an indenyl group, a substituted indenyl group having at least one substituent selected from the group consisting of hydrocarbon groups and silicon-containing hydrocarbon groups, a fluorenyl group or a substituted fluorenyl group having at least one substituent selected from the group consisting of hydrocarbon groups and silicon-containing hydrocarbon groups; O represents an oxygen atom; X represents a hydrogen atom, a halogen atom, a hydrocarbon group having 1 to 20 carbon atoms, an alkoxy group, an aryloxy group or an amido group; L represents a Lewis basic compound; n, m, and p each represent an integer selected to make a combination of (n=1, m=1, p=2), (n=1, m=0, p=3), (n=2, m=0, p=1) or (n=1, m=0, p=2); and a represents 0, 1 or 2, and (B) at least one of (B1) an ionic compound comprising a non-coordinating anion and a cation and (B2) an aluminoxane, provided that said component (B) is an ionic compound comprising a non-coordinating anion and a cation (B1) when the combination of n, m, and p of said component (A) is (n=2, m=0, p=1) or (n=1, m=0, p=2).

7. A catalyst as claimed in claim 6, wherein said catalyst further comprises (C) an organic compound of the group I, II or III metal of the Periodic Table.

8. A catalyst obtained by contacting:

(A) a compound of a transition metal of the group V of the Periodic Table represented by the formula $RM(O)X_2$, wherein M represents a transition metal of the group V of the Periodic Table; R represents a cyclopentadienyl group, a substituted cyclopentadienyl group, an indenyl group, a substituted indenyl group, a fluorenyl group or a substituted fluorenyl group; O represents an oxygen atom; and X represents a hydrogen atom, a halogen atom, a hydrocarbon group having 1 to 20 carbon atoms, an alkoxy group, an aryloxy group or an amido group; and (B) at least one of (B1) an ionic compound comprising a non-coordinating anion and a cation and (B2) an aluminoxane.

9. A catalyst obtained by contacting:

(A) a compound of a transition metal of the group V of the Periodic Table represented by the formula $R_nMX_p \cdot L_a$, wherein the combination of (n, p) is (n=2, p=1) or (n=1, p=2); a is 0, 1 or 2; and M represents a transition metal of the group V of the Periodic Table; R represents a cyclopentadienyl group, a substituted cyclopentadienyl group, an indenyl group, a substituted indenyl group, a fluorenyl group or a substituted fluorenyl group; X represents a hydrogen atom, a halogen atom, a hydrocarbon group having 1 to 20 carbon atoms, an alkoxy group, an aryloxy group or an amido group; and L represents a Lewis basic compound; and (B1) an ionic compound comprising a non-coordinating anion and a cation.

10. A conjugated diene polymerization catalyst obtained by contacting:

(A) a compound of a transition metal of the group V of the Periodic Table represented by the formula (I);

(I)

wherein M represents a transition metal of the group V of the Periodic Table; R represents a cyclopentadienyl group, a substituted cyclopentadienyl group having at least one substituent selected from the group consisting of hydrocarbon groups and silicon-containing hydrocarbon groups, an indenyl group, a substituted indenyl group having at least one substituent selected from the group consisting of hydrocarbon groups and silicon-containing hydrocarbon groups, a fluorenyl group or a substituted fluorenyl group having at least one substituent selected from the group consisting of hydrocarbon groups and silicon-containing hydrocarbon groups; O represents an oxygen atom; X represents a hydrogen atom, a halogen atom, a hydrocarbon group having 1 to 20 carbon atoms, an alkoxy group, an aryloxy group or an amido group; L represents a Lewis basic compound; n, m, and p each represent an integer selected to make a combination of (n=1, m=1, p=2), (n=1, m=0, p=3), (n=2, m=0, p=1) or (n=1, m=0, p=2); and a represents 0, 1 or 2, and (B) at least one of (B1) an ionic compound comprising a non-coordinating anion and a cation and (B2) an aluminoxane, provided that said component (B) is an ionic compound comprising a non-coordinating anion and a cation (B1) when the combination of n, m, and p of said component (A) is (n=2, m=0, p=1) or (n=1, m=0, p=2).

* * * * *